United States Patent
Jarc et al.

(10) Patent No.: US 10,510,267 B2
(45) Date of Patent: Dec. 17, 2019

(54) SIMULATOR SYSTEM FOR MEDICAL PROCEDURE TRAINING

(71) Applicant: INTUITIVE SURGICAL OPERATIONS, INC., Sunnyvale, CA (US)

(72) Inventors: Anthony M. Jarc, Sunnyvale, CA (US); Joey Chau, Cupertino, CA (US); Brian E. Miller, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 374 days.

(21) Appl. No.: 15/106,254

(22) PCT Filed: Dec. 19, 2014

(86) PCT No.: PCT/US2014/071521
§ 371 (c)(1),
(2) Date: Jun. 17, 2016

(87) PCT Pub. No.: WO2015/095715
PCT Pub. Date: Jun. 25, 2015

(65) Prior Publication Data
US 2016/0314710 A1   Oct. 27, 2016

Related U.S. Application Data

(60) Provisional application No. 61/919,631, filed on Dec. 20, 2013.

(51) Int. Cl.
*G09B 23/28* (2006.01)
*A61B 34/30* (2016.01)

(52) U.S. Cl.
CPC .......... *G09B 23/28* (2013.01); *G09B 23/285* (2013.01); *A61B 34/30* (2016.02)

(58) Field of Classification Search
None
See application file for complete search history.

(56) References Cited

U.S. PATENT DOCUMENTS

| 4,321,047 A | 3/1982 | Landis |
| 5,403,191 A | 4/1995 | Tuason |

(Continued)

FOREIGN PATENT DOCUMENTS

| CN | 102362302 A | 2/2012 |
| JP | 2006087936 A | 4/2006 |

(Continued)

OTHER PUBLICATIONS

Extended European Search Report for Application No. 14871282.1, dated Jun. 7, 2017, 7 pages.

(Continued)

*Primary Examiner* — Samchuan C Yao
*Assistant Examiner* — Joshua S Luo
(74) *Attorney, Agent, or Firm* — IP Spring

(57) ABSTRACT

Implementations relate to medical simulations for medical procedure training. In some implementations, a system includes a simulation processing component including at least one processor and which generates a virtual environment using position signals that describe at least one of a position and a configuration of a physical surgical instrument relative to a physical surgical site. The simulation processing component updates the virtual environment according to changes in the position signals and according to control signals corresponding to inputs by a user of the system. The updating includes moving a virtual surgical instrument within the virtual environment, where an interaction of the virtual surgical instrument with a virtual surgical site is defined at least partly by a physical relationship between the physical surgical instrument and the physical surgical site. The simulation processing component outputs a representation of a simulation state signal indicative of a current state of the virtual environment.

19 Claims, 14 Drawing Sheets

(56) References Cited

U.S. PATENT DOCUMENTS

| | | | |
|---|---|---|---|
| 5,620,326 A | 4/1997 | Younker | |
| 5,766,016 A | 6/1998 | Sinclair et al. | |
| 5,769,640 A | 6/1998 | Jacobus et al. | |
| 5,800,177 A | 9/1998 | Gillio | |
| 5,945,056 A | 8/1999 | Day et al. | |
| 5,951,301 A | 9/1999 | Younker | |
| 6,024,576 A * | 2/2000 | Bevirt | G05G 9/04 345/158 |
| 6,377,011 B1 | 4/2002 | Ben-Ur | |
| 6,544,041 B1 | 4/2003 | Damadian | |
| 7,798,815 B2 | 9/2010 | Ramphal et al. | |
| 7,866,983 B2 | 1/2011 | Hemphill et al. | |
| 8,190,238 B2 | 5/2012 | Moll et al. | |
| 8,469,716 B2 | 6/2013 | Fedotov et al. | |
| 8,600,551 B2 * | 12/2013 | Itkowitz | G09B 23/285 700/245 |
| 8,786,675 B2 | 7/2014 | Deering | |
| 9,196,176 B2 * | 11/2015 | Hager | G09B 7/00 |
| 2004/0045561 A1 * | 3/2004 | Alexander | G09B 23/285 128/897 |
| 2004/0126746 A1 | 7/2004 | Toly | |
| 2005/0142525 A1 * | 6/2005 | Cotin | G09B 23/285 434/262 |
| 2006/0019228 A1 | 1/2006 | Riener et al. | |
| 2006/0073454 A1 * | 4/2006 | Hyltander | G09B 23/285 434/262 |
| 2006/0099557 A1 * | 5/2006 | Hyltander | G09B 23/28 434/262 |
| 2007/0275359 A1 | 11/2007 | Rotnes et al. | |
| 2007/0292829 A1 | 12/2007 | King et al. | |
| 2007/0293734 A1 | 12/2007 | Coste-Maniere et al. | |
| 2008/0187896 A1 * | 8/2008 | Savitsky | G09B 23/28 434/272 |
| 2008/0227073 A1 | 9/2008 | Bardsley et al. | |
| 2009/0132925 A1 | 5/2009 | Koehler et al. | |
| 2009/0142739 A1 | 6/2009 | Wang et al. | |
| 2009/0176196 A1 | 7/2009 | Niblock et al. | |
| 2009/0253109 A1 | 10/2009 | Anvari et al. | |
| 2009/0263775 A1 * | 10/2009 | Ullrich | G09B 23/285 434/267 |
| 2009/0317002 A1 | 12/2009 | Dein | |
| 2009/0326324 A1 * | 12/2009 | Munoz Martinez | A61B 34/30 600/118 |
| 2010/0035223 A1 | 2/2010 | Shibui et al. | |
| 2010/0086905 A1 | 4/2010 | Illana et al. | |
| 2010/0099066 A1 | 4/2010 | Mire et al. | |
| 2010/0167248 A1 * | 7/2010 | Ryan | G09B 23/28 434/262 |
| 2010/0167249 A1 * | 7/2010 | Ryan | G09B 23/285 434/267 |
| 2010/0167250 A1 * | 7/2010 | Ryan | G09B 23/285 434/267 |
| 2010/0167253 A1 | 7/2010 | Ryan et al. | |
| 2010/0216105 A1 | 8/2010 | Hammerman | |
| 2010/0234857 A1 * | 9/2010 | Itkowitz | G09B 23/285 606/130 |
| 2010/0311028 A1 * | 12/2010 | Bell, III | G09B 23/28 434/263 |
| 2011/0014596 A1 * | 1/2011 | Kurenov | G09B 23/285 434/262 |
| 2011/0046935 A1 * | 2/2011 | Sugaya | G06F 19/3481 703/11 |
| 2011/0086332 A1 * | 4/2011 | Speiser | G09B 23/285 434/219 |
| 2011/0117530 A1 * | 5/2011 | Albocher | G16H 50/50 434/267 |
| 2011/0152882 A1 | 6/2011 | Wenderow et al. | |
| 2011/0212426 A1 * | 9/2011 | Gloeggler | G09B 23/285 434/262 |
| 2011/0256519 A1 | 10/2011 | Park et al. | |
| 2012/0045742 A1 * | 2/2012 | Meglan | G09B 23/28 434/268 |
| 2012/0053402 A1 | 3/2012 | Conlon et al. | |
| 2012/0058457 A1 * | 3/2012 | Savitsky | G09B 23/286 434/262 |
| 2012/0082970 A1 | 4/2012 | Pravong et al. | |
| 2012/0115118 A1 | 5/2012 | Marshall | |
| 2012/0135387 A1 | 5/2012 | Morrow et al. | |
| 2012/0148994 A1 | 6/2012 | Hori et al. | |
| 2012/0189996 A1 * | 7/2012 | Hager | G09B 7/00 434/262 |
| 2012/0251987 A1 | 10/2012 | Huang et al. | |
| 2012/0264096 A1 * | 10/2012 | Taylor | G09B 23/28 434/262 |
| 2012/0264097 A1 | 10/2012 | Newcott et al. | |
| 2012/0282583 A1 * | 11/2012 | Thaler | G09B 23/28 434/267 |
| 2013/0101973 A1 | 4/2013 | Hoke et al. | |
| 2013/0157240 A1 | 6/2013 | Hart et al. | |
| 2013/0189663 A1 * | 7/2013 | Tuchschmid | G09B 23/28 434/262 |
| 2013/0192741 A1 | 8/2013 | Trotta et al. | |
| 2013/0218340 A1 * | 8/2013 | Hager | B25J 9/1671 700/257 |
| 2013/0230837 A1 * | 9/2013 | Meglan | G09B 23/28 434/262 |
| 2013/0288217 A1 | 10/2013 | Hammerman | |
| 2013/0295540 A1 * | 11/2013 | Kesavadas | G09B 23/28 434/262 |
| 2014/0011172 A1 | 1/2014 | Lowe | |
| 2014/0051049 A1 | 2/2014 | Jarc et al. | |
| 2014/0057236 A1 * | 2/2014 | Meglan | G09B 23/30 434/268 |
| 2014/0087346 A1 | 3/2014 | Breslin et al. | |
| 2014/0087347 A1 | 3/2014 | Tracy et al. | |
| 2014/0087348 A1 | 3/2014 | Tracy et al. | |
| 2014/0093854 A1 | 4/2014 | Poulsen et al. | |
| 2014/0106328 A1 | 4/2014 | Loor | |
| 2014/0272878 A1 | 9/2014 | Shim et al. | |
| 2014/0272879 A1 | 9/2014 | Shim et al. | |
| 2014/0287393 A1 * | 9/2014 | Kumar | G09B 23/28 434/262 |
| 2014/0329217 A1 | 11/2014 | Barsness et al. | |
| 2015/0037775 A1 * | 2/2015 | Ottensmeyer | G09B 23/34 434/271 |
| 2015/0100066 A1 * | 4/2015 | Kostrzewski | A61B 34/30 606/130 |
| 2015/0132732 A1 | 5/2015 | Hart et al. | |
| 2015/0262511 A1 * | 9/2015 | Lin | G09B 23/28 434/262 |
| 2015/0325151 A1 * | 11/2015 | Tuchschmid | A61B 34/20 434/267 |
| 2015/0356891 A1 * | 12/2015 | Will | G09B 23/285 434/272 |
| 2016/0098933 A1 | 4/2016 | Reiley et al. | |
| 2016/0321956 A1 | 11/2016 | Jarc | |
| 2016/0379504 A1 * | 12/2016 | Bailey | G09B 5/02 434/219 |

FOREIGN PATENT DOCUMENTS

| | | |
|---|---|---|
| JP | 2007007041 A | 1/2007 |
| JP | 2009529951 A | 8/2009 |
| JP | 2009236963 A | 10/2009 |
| JP | 2012521568 A | 9/2012 |
| KR | 20110065388 A | 6/2011 |
| KR | 20120122542 A | 11/2012 |
| WO | WO-0030548 A1 | 6/2000 |
| WO | WO-2006060406 A1 | 6/2006 |
| WO | WO-2009094621 A2 | 7/2009 |
| WO | WO-2010105237 A2 | 9/2010 |

OTHER PUBLICATIONS

International Preliminary Report on Patentability for Application No. PCT/US2014/071521, dated Jun. 30, 2016, 7 pages.
International Search Report and Written Opinion for Application No. PCT/US14/71521, dated Mar. 31, 2015, 11 pages.

(56) References Cited

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Feb. 20, 2019 for Chinese Application No. 201480076076 filed Dec. 19, 2014, 25 pages.

\* cited by examiner

SIMULATOR SYSTEM FOR MEDICAL PROCEDURE TRAINING

RELATED APPLICATIONS

This application is the U.S. national phase of International Application No. PCT/US2014/071521, filed Dec. 19, 2014, which designated the U.S. and claims priority to U.S. provisional patent application 61/919,631, filed on Dec. 20, 2013, the contents of each of which are incorporated herein by reference.

BACKGROUND

Disclosed features concern medical training equipment and methods, and more particularly medical training equipment and methods used for training in minimally invasive surgical procedures and techniques.

Medical procedures on patients can involve a variety of different tasks by one or more medical personnel. Some medical procedures are minimally-invasive surgical procedures performed using one or more devices, including teleoperated medical devices. In some such systems, a surgeon operates controls via a console, which remotely and precisely control surgical instruments that interact with the patient to perform surgery and other procedures. In some systems, various other components to the system can also be used to perform a procedure. For example, the surgical instruments can be provided on a separate instrument device or cart that is positioned near or over a patient, and a video output device and other equipment and devices can be provided on one or more additional units.

Systems have been developed to provide certain types of training in the use of a teleoperated medical system. A simulator unit, for example, can be coupled to a surgeon console instead of the actual other system components, to provide a surgeon with a simulation of performing the procedure. With such a system, the surgeon can learn how simulated instruments respond to manipulation of the console controls.

However, surgeons and various other personnel may perform tasks on other components of the teleoperated medical system during a medical procedure. For example, assistants may move and position teleoperated arms and instruments of an instrument unit in the correct positions, which can have a significant effect on the procedure. It can be beneficial for assistants to also be able to find needed information quickly during a procedure.

In addition, it can be beneficial to quantify training and performance of such tasks by surgeons and assistants, thereby enabling such personnel to track progress and improve performance.

SUMMARY

Implementations of the present application relate to medical simulations for medical procedure training. In some example implementations, a system includes a simulation processing component including at least one processor and generating a virtual environment using position signals that describe at least one of a position and a configuration of a physical surgical instrument relative to a physical surgical site. The simulation processing component updates the virtual environment according to changes in the position signals and according to control signals corresponding to inputs by a user of the system. The updating of the virtual environment comprises moving a virtual surgical instrument within the virtual environment, where an interaction of the virtual surgical instrument with a virtual surgical site of the virtual environment is defined at least partly by a physical relationship between the physical surgical instrument and the physical surgical site. The simulation processing component outputs a representation of a simulation state signal indicative of a current state of the virtual environment. Various implementations can include a dummy instrument, anatomical model, control console, display device, teleoperable medical device, and/or other variations.

In some example implementations, a method includes coordinating a simulated medical procedure using a simulation processing component and receiving position signals based on one or more positions of elements of a teleoperable medical device moved by at least one trainee during the simulated medical procedure. The elements are physically positionable relative to a physical surgical site in order to perform the simulated medical procedure. Simulation state signals are determined based on the position signals, where the simulation state signals are indicative of a current state of the simulated medical procedure including integration of the position signals from the teleoperable medical device. The simulation state signals are sent to at least one output device operative to output a representation of the simulation state signals. Various implementations of the method can include receiving the position signals in a simulated setup procedure for setup tasks performed by a trainee, and/or in a simulated surgical operation following the simulated setup procedure, outputting real-time feedback information to at least one trainee performing the tasks, and other variations.

In some example implementations, a method includes receiving position signals indicating positions of one or more physical surgical instruments relative to a physical simulated surgical site in a simulated medical procedure. A virtual environment is updated based on the position signals, where the virtual environment implements a virtual surgical site corresponding to the physical surgical site. Control signals are received from a control console and indicate manipulation of one or more input controls of the control console by a user. The method updates the virtual environment based on the control signals, including moving one or more virtual surgical instruments within the virtual environment. Interaction of the virtual instruments with the virtual surgical site are based on the positions of the one or more physical surgical instruments relative to the physical surgical site. Simulation state signals are output to at least one output device to cause output of a representation of the simulation state signals, where the simulation state signals are indicative of a current state of the virtual environment. Various implementations of the method can include physical surgical instruments being coupled to associated manipulator arms of a teleoperated medical device, or physical surgical instruments being manually operated by one or more users relative to a physical anatomical model, and other variations.

DETAILED DESCRIPTION

Figure 1:
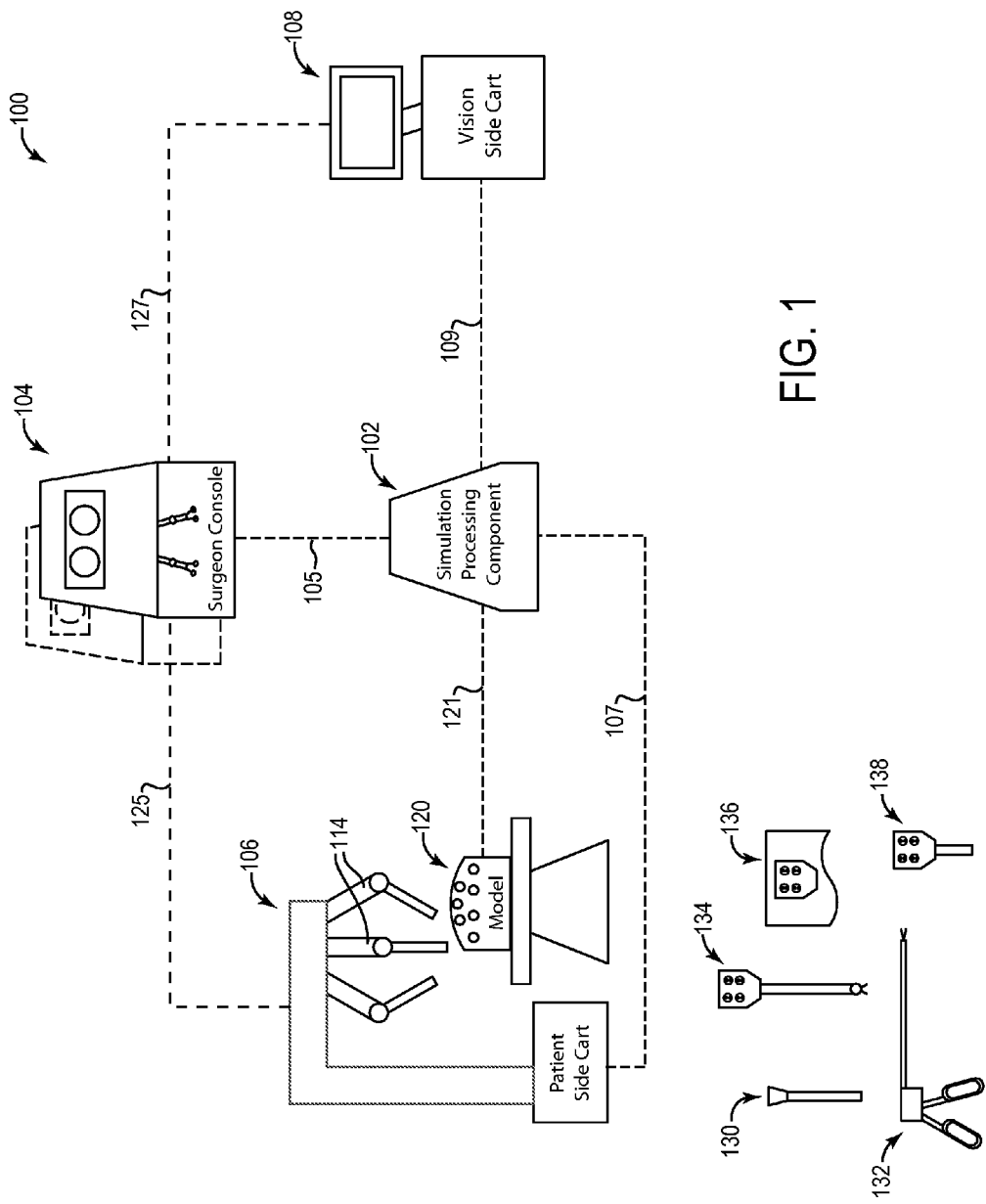
FIG. 1 is a diagrammatic illustration of an example simulation system including a teleoperated medical system, according to some implementations.

The present application discloses features relating to simulated surgical procedures and training exercises. Various disclosed implementations of simulation systems and methods provide and teach realistic setup procedures for positioning, placement of simulation equipment for particular surgical procedures, as well as the realistic use of such equipment for the actual surgical operation. Simulations can involve some or all of the components involved in every stage of actual medical procedures and can involve any personnel in such procedures, to provide highly realistic training. Various tasks performed during all of these simulated medical procedures can be recorded and evaluated, with appropriate feedback on performances provided, allowing a high degree of analysis in the details of the procedures and enabling trainees for every function of a medical procedure to improve their skills more efficiently. Various simulation features described herein can allow users to learn and practice, and can allow quantification of user performance and tracking of user progress.

Some implementations are described using a teleoperated medical system such as a da Vinci® Surgical System (e.g., a Model IS3000, marketed as the da Vinci® Si™ HD™ Surgical System), commercialized by Intuitive Surgical, Inc. of Sunnyvale, Calif. Knowledgeable persons will understand, however, that features disclosed herein may be embodied and implemented in various ways, including teleoperated and, if applicable, non-teleoperated (e.g., manual) embodiments and implementations. Implementations on da Vinci® Surgical Systems (e.g., the Model IS3000; the Model IS2000, commercialized as the da Vinci® S™ HD™ Surgical System) are merely exemplary and are not to be considered as limiting the scope of the inventive aspects disclosed herein.

Herein, a "setup procedure" or "surgical setup procedure" refers to setup tasks that configure system components to perform one or more later surgical operations. A "surgical operation" or "surgical site procedure" refers to the actual surgical operation including surgical tasks at a surgical site. A "simulated medical procedure" or "simulated surgical procedure" can refer to the entire simulated procedure including setup procedure and surgical operation, or can include just setup procedure or surgical operation. The term "teleoperated medical system" refers to a system of one or more components used to perform surgical procedures using one or more master controller devices and one or more slave teleoperated medical devices. A "teleoperated medical device" can be a slave device controlled by a remote master device and can include one or more elements, such as manipulator arms and/or surgical instruments, that can be moved or manipulated in response to signals provided by one or more of the master controller devices, such as a control console or surgeon console operated by a user remotely from the teleoperated medical device. A "wet-lab" exercise refers to any exercise on actual (real) tissue, such as tissue samples, a porcine model, or cadaver. A "dry-lab" exercise refers to an exercise using non-tissue models or objects, including "inanimate" exercises using objects such as foam (for suturing), rings on wires, etc.

FIG. 1 is a diagrammatic illustration of an example simulation system 100 including a teleoperated medical system, according to some implementations. Simulation system 100 can be used to simulate actual medical procedures without using actual patients. Any simulated medical procedure or training activity that does not take place on an actual human patient can be performed using simulation system 100 or a variation thereof. For example, simulations of dry-lab training tasks (e.g., inanimate exercises) and/or wet-lab training tasks (e.g., exercises on real tissue, porcine model, or cadaver) can be performed.

In the example shown, simulation system 100 can include a simulation processing component (or "processing component") 102, a surgeon console 104, a patient side cart 106, and a vision side cart 108. Other components can additionally or alternatively be included in the simulation system 100, as described in various implementations herein.

Simulation processing component 102 can coordinate, control, and/or implement a simulation that involves the various other components of the simulation system 100. The simulation simulates a medical procedure environment involving the system components as if an actual patient were to be, or being, operated upon. In some implementations, the simulation processing component implements and controls the display of a virtual environment that includes a virtual surgical site depicting one or more elements of an actual physical surgical site. Some implementations can include a physical surgical site that includes a physical model and/or objects.

In some implementations, the processing component 102 can coordinate simulation components of the simulation system and/or monitor and record parameters obtained during simulated medical procedures.

The simulation is an interactive one that involves the simulation processing component 102 receiving a number of inputs from the other components of the system based on user manipulation of those components within the simulation. The simulation processing component also provides a number of outputs based on those inputs, where the outputs can coordinate the components of the simulation system and provide output to users of the system via any of different types of output devices (display screens, audio speakers, motors, etc.) provided on one or more of the components of the system 100. For example, the simulation processing component can provide output to users via simulation state signals provided to one or more output devices. The simulation processing component can also provide feedback information to users via signals that it outputs.

The simulation state signals can be indicative of a current state of the simulated medical procedure including integration of (e.g., influence from) inputs from one or more system components. The current "state" of the simulated medical procedure is the current point of progress or status in the performance of the medical procedure as influenced by the inputs of the components of the simulation system. For example, in some implementations simulation state signals can indicate the current positions of physical teleoperated surgical instruments of a teleoperated medical device of patent side cart 106 with respect to a physical surgical site, where these current instrument positions indicate the current state of progress in positioning the surgical instruments relative to the site in the simulated medical procedure, e.g., in a setup procedure. For example, the simulation state signals can also indicate events in the medical procedure, such as collisions of any instruments with other instruments or surfaces, or mis-positioning of component elements. In some implementations, the current state of the simulated medical procedure can include a current state of a virtual environment, such as a virtual surgical site, implemented by the simulation processing component. For example, the simulation state signals can include data that describes the virtual environment including virtual representations and current positions of surgical instruments. Simulation state signals can indicate current positions of virtual surgical instruments in the virtual environment based on control input from a surgeon console 102, where the positions of the virtual surgical instruments indicate the current state of a surgical task of a simulated medical procedure.

The output device(s) can output a representation of the simulation state signals. The representation can be output using a variety of types of output, such as graphical (e.g., fully virtual/synthetic images, fully camera images, or combined camera/virtual images), tactile, haptic, aural, etc. For example, in a simulated setup procedure, the output representation can include graphical representations of physical instruments, displayed visual statuses, notifications, visual text and markers, audio cues and other output, haptic responses, and/or other output. During a simulated surgical operation, the output representation can include a displayed environment at the surgical site, such as a virtual environment or images of a physical site. In some examples, an initial state of a virtual environment can be selected by the simulation processing component by providing various controlling output signals to the other components, and users can experience current updates to the virtual environment via the state simulation signals based on user inputs via components such as the surgeon console 104 and/or patient side cart 106. The output device(s) can also output representations of signals providing feedback information.

The simulation processing component 102 can be implemented using one or more processors (e.g., microprocessors, integrated circuits, logic, and/or other processing circuitry), as well as memory, input/output interfaces, and other components, as described below. In some implementations, simulation processing component 102 can be implemented as a particular external or standalone unit that is separate from the other components in the simulation system. In other implementations, the processing component 102 can be provided within or a part of one of the other components of the simulation system 100, and/or distributed within multiple other components of the system 100.

One or more master consoles 104, such as a surgeon console or control console, can be included in system 100 to provide a user, such as a surgeon trainee, input controls by which surgical instruments can be teleoperated as well as various other controls. Surgeon console 104 can also include output devices such as visual, audio, and/or haptic output devices. A user operates the controls to provide control input signals to the simulation processing component. Control input signals can also be provided from a surgeon console 104 to one or more of the other components of the simulation system, such as the patient side cart 106 and/or vision side cart 108. For example, teleoperated slave instrument arms of the patient side cart 106 can be controlled, e.g., each surgical instrument operated by one or more corresponding master controls of the surgeon console. Some examples of such teleoperated medical devices and surgical instruments are described below.

The surgeon console 104 communicates with the simulation processing component 102 as indicated by connection 105. Connection 105 can be any type of communication channel, such as one or more wires or cables, wireless connections, etc. The surgeon console 104 outputs signals indicative of the manipulation of the controls of the console 104. For example, if a user moves levers, joysticks, or dials, selects particular buttons or touchscreen, or selects other controls, corresponding signals are provided to the simulation processing component 102. In some implementations, these signals can be standard signals provided to the other components of a teleoperated medical system during an actual medical procedure, such as patient side cart 106 and/or vision side cart 108, where the simulation processing component 102 can process these same signals. In other implementations, simulation signals which are specific to the simulation can be output by the surgeon console 104. The simulation processing component 102 can use the inputs to update a virtual environment of the simulation, for example.

In some implementations, the surgeon console 104 also can output signals to one or more components of the simulation system 100, such as the patient side cart 106 and/or the vision side cart 108. For example, signals received by the simulation processing component 100 can be relayed to these other components by the simulation processing component. Alternatively, the surgeon console 104 can have separate, direct connections similar to connection 105 with one or more of the other components of the simulation system. The output signals can drive the operation of these other components similarly to a teleoperated medical system that does not use a simulation processing component 102.

In addition, the surgeon console 104 receives signals on connection 105 from the simulation processing component 102. These received signals include signals that would normally be received by the surgeon console 104 in an actual medical procedure, including simulation state signals used to update visual, audio, and/or haptic output devices of the surgeon console that provide a representation of the simulation state signals via video, audio, and haptic output to its user. In some implementations, these signals can be generated by the simulation processing component 102 to describe a current state of a simulated, virtual environment provided by the simulation processing component 102 and displayed at the surgeon console. In some implementations, received signals can include signals provided by one or more of the other components of the simulation system, such as signals received at the simulation processing component 102 from the patient side cart 106 and/or the vision side cart 108 and then relayed to the surgeon console 104 from the simulation processing component 102. In still other implementations, the simulation processing component 102 can receive signals from one or more of the other components and can process or change these signals based on the simulation run by the simulation processing component. The processed signals can then be sent to the surgeon console 104 for its use. In some examples, the simulation processing component 102 can create augmented reality data that is combined with or integrated into data received from the other components of the simulation system such as an image or video feed from an endoscope or other imaging device at the surgical site, and the combined data can then be sent to the surgeon console 104 as simulation state signals. In some implementations, the surgeon console 104 can have additional separate, direct connections similar to connection 105 with one or more of the other components of the simulation system to receive the signals from those other components similarly to a teleoperated medical system that does not use a simulation processing component 102.

In some implementations, multiple master consoles 104 can be in communication with the simulation processing component 102. For example, such multiple consoles can be each be operated by a dedicated user simultaneously during a medical procedure, e.g., to have each user control particular device instruments, to have one user assist the other in surgical exercises, etc. Each such surgeon console 104 can send signals to the simulation processing component 102 and can receive signals from the simulation processing component, e.g., describing a virtual environment. Some simulation implementations can allow a user at a console 104 to pass control of one or more surgical instruments (virtual and/or physical) or pass control of other components or inputs to a different user of a different console 104, e.g. by sending a command to pass control via input controls of a console 104 or other device (e.g., other control panel in system 100). In some cases, signals appropriate to each surgeon console can be received at that console, e.g., outputting a different visual perspective on a simulated surgical site at each console 104 based on which instruments that the particular console controls. Some implementations can include features specific to simulations having more than one console 104. For example, virtual pointers can be generated and displayed on display screens of the consoles 104, where one operator at one console 104 (e.g. an expert) can control the pointer and point to displayed objects as viewed by the other operator at the other console 104 (e.g., a new trainee).

One or more patient side carts 106 can be included in simulation system 100 to provide realistic physical interactions of controlled devices that are made during an actual teleoperated medical procedure. For example, one or more users such as trainee assistants who operate the patient side cart 106 can be trained during a simulated medical procedure using the actual patient-side devices used in teleoperated medical procedures. Some trainees (e.g., other, surgeon trainees) can be trained to operate the surgeon console 104 to control the patient side cart 106, such as moving physical teleoperated arms or other elements and/or other functions. Such features enable users to be realistically, accurately, and effectively trained during simulated medical procedures.

The patient side cart 106 can be a standalone device separate from the other components of the system 100. Cart 106 can include a variety of different mechanisms and devices to enable teleoperated medical surgery on patients. In some examples, the cart 106 includes one or more manipulable elements, such as multiple controlled manipulator arms 114 that each can have one or more surgical instruments removably the attached thereto. Such arms and their surgical instruments can be driven within particular ranges and modes of motion such as to allow a user of the surgeon console 104 to manipulate the instruments to perform a surgical medical operation on a patient. For example, actuators (e.g., motors) in the arms and/or instruments of the cart 106 can be controlled by signals from the console 104 and can drive movement of the instruments to perform surgical tasks.

In some implementations, additional patient side carts 106 can be included in simulations. Some patient side carts can include teleoperated medical devices, while others can include other types of devices (other surgical instruments, video displays, operating room tables, etc.). Still others can include both teleoperated medical devices and non-teleoperated devices.

A trainee user of the patient side cart 106 can perform a setup procedure involving the cart 106 to permit a (e.g. simulated) surgical operation to take place. For example, this setup procedure can include tasks such as moving the cart to a proper position, and moving each arm 114 to a proper position. In some implementations, the setup of the patient side cart 106 can be with reference to a physical anatomical model 120. For example, the anatomical model 120 can simulate a portion of a human patient or other subject, and can include various features allowing the surgical instruments of the patient side cart 106 to be positioned properly. In some examples, to further set up the cart 106, the user places surgical instruments of the cart 106 within appropriate apertures of the anatomical model 120 (e.g., designated via port placement), so that the instruments obtain access to a physical surgical site simulated within the interior of the model 120. Other setup tasks may also be performed, such as installing the correct surgical instruments on the arms 114, selecting and operating particular controls of the cart 106 to enable needed functions, adjusting the positing of the manipulator arms to achieve patient clearance or avoid collisions, etc.

The patient side cart 106 communicates with the simulation processing component 102 as indicated by connection 107. Connection 107 can be any type of communication channel, such as one or more wires or cables, wireless connections, etc. The patient side cart 106 can receive signals from the simulation processing component 102 which control its teleoperated functions, such as the movement of arms 114 and the manipulation of surgical instruments attached to the arms 114 and/or otherwise coupled to the cart 106. In addition, the patient side cart 106 can receive other signals such as simulation state signals (e.g., data) creating output from visual, audio, or other output devices on the cart 106 to the user of the cart. In some examples, signals received by the patient side cart 106 can be generated by the simulation processing component 102 based on an implemented virtual environment, and/or can be provided by the surgeon console and passed through to the cart 106 by the simulation processing component 102.

The patient side cart 106 also sends signals on connection 107 to the simulation processing component 102. Such signals can include data describing the current states of the cart 106, including positions and orientations of the arms 114 and surgical instruments of the cart 106 as determined by sensors of the cart 106. For example, joint position sensors, servo motor position encoders, fiber Bragg grating shape sensors, etc. can be used to determine kinematic information (position and/or orientation) associated with the manipulator arms. The signals can also include data describing a visual image of the physical surgical site as captured by an endoscope or other imaging instrument of the patient side cart 106 and/or other images describing the surgical site or simulated patient (e.g., rendered ultrasound images, patient vital signs, etc.). Other signals can also be sent, such as input data describing the cart user's actions or messages, audio data from a microphone or generated by interactions of the cart's devices, and other forms of data. Various other signals describing states can also be sent, such as the states of particular cart controls, functions, etc. In some implementations, these signals can be standard signals provided to the surgeon console 104 of a teleoperated medical system for an actual medical procedure, where the simulation processing component 102 can process these same signals. In other implementations, simulation signals specific to a simulation can be output by the patient side cart 106. The simulation processing component 102 can use the signals to update the virtual environment of the simulation, for example.

In some implementations, the patient side cart 106 can send its signals to the simulation processing component 102, which generates appropriate signals in response which are sent to the surgeon console. In some cases or implementations, the simulation processing component can relay one or more of the signals from cart 106 directly to the surgeon console 104 via connection 125. In still other implementations, the patient side cart 106 can have additional direct connections to the surgeon console 104, vision side cart 108, and/or other system components.

In some implementations, the anatomical model 120 can include its own sensors and can provide signals to and/or receive signals from the simulation processing component 102 on a connection similar to connection 107. For example, a connection 121 can provide signals between the anatomical model 120 and the simulation processing component 102. Alternatively, the model 120 can connect to patient side cart 106 which can relay signals between the model 120 and simulation processing component 102. Such sensors on the model 120 can allow manual surgical instruments to be tracked by the simulation, as described in greater detail below.

Some implementations of system 100 can include other operating room equipment (e.g., operating table supporting the model 120, assistive tables or carts for additional surgery or support functions, etc.) which can include connections and communication to the simulation processing component 102 similarly to the anatomical model 120. For example, such other equipment can be included in and its use evaluated for simulation tasks and procedures described herein.

One or more vision side carts 108 can be included in some implementations of simulation system 100 to provide output information to assistant users of the simulation system, and/or to hold equipment such as vision and data processing hardware. The vision side cart 108 can be a standalone device separate from the other components of the system 100. For example, in some teleoperated medical systems, a vision side cart 108 can be used by an assistant, such as the assistant that sets up and operates the patient side cart 106. The vision side cart 108 includes one or more visual output devices, such as display screens, which can output a variety of information useful to the medical procedure being performed. For example, the display screen can display a view of the surgical site as captured by an endoscopic camera provided on a surgical instrument of the patient side cart 106, which allows the assistant user to adjust the camera to positions needed for the surgical operation. The display screen can also display other output information such as the states of one or more controls being activated by the surgeon at the surgeon console, the states of other devices used in the medical procedure, etc.

The vision side cart 108 communicates with the simulation processing component 102 as indicated by connection 109. Connection 109 can be any type of communication channel, such as one or more wires or cables, wireless connections, etc. The vision side cart 108 can receive signals from the simulation processing component 102 which control its functions, such as simulation state signals causing display of a virtual environment simulating the surgical site or display of images captured at the physical surgical site, display of status information related to various system components, and output of any other types of output (audio, haptic, etc.) via appropriate output devices of the cart 108. In addition, the vision side cart 108 can receive such signals provided by the surgeon console 104 and relayed through to the cart 108 by the simulation processing component 102.

The vision side cart 108 also sends signals on connection 109 to the simulation processing component 102 and/or other components of the system 100. Such signals can include data describing the current states of controls or other input devices on the vision side cart which were activated by a user. The signals can include data received by the vision side cart 108 from other components such as patient side cart 106 and relayed by the cart 108 to the simulation processing component 102 and/or surgeon console 104. In some implementations, signals output by cart 108 can be standard signals provided to the surgeon console 104 of a teleoperated medical system, where the simulation processing component 102 can process these same signals. In other implementations, specific simulation signals can be output by the vision side cart 108. The simulation processing component 102 can use the signals to update the virtual environment of the simulation, for example. In some implementations, the vision side cart 108 can send its signals to the simulation processing component 102, which generates appropriate signals in response which are sent to the surgeon console 104 and/or to the patient side cart 106. In some cases or implementations, the simulation processing component 102 can relay one or more of the signals from cart 108 directly to other components, such as to the surgeon console 104 via connection 127. In still other implementations, the vision side cart 108 can have additional direct connections to the surgeon console 104, patient side cart 106, and/or other components.

In some implementations, a variety of physical surgical instruments can be used by the simulation system 100 to more fully simulate an actual medical procedure. These surgical instruments can include complete, actual surgical instruments that are used in the actual medical procedure being simulated. For example, standard manual surgical instruments such as a cannula 130 and laparoscopic instrument 132 can be used, which can be instruments not requiring the teleoperated patient side cart 106. Furthermore, surgical instruments used with the patient side cart 106, such as surgical instrument 134 and sterile adapter/drape instrument 136 can be used, which are removably attached to teleoperated manipulator arms of the patient side cart 106.

Some implementations of simulation system 100 can also or alternatively use non-operational "fake" surgical instruments 138. These can be instruments that are dummies used only for the simulation system and do not provide the full instrument functionality. For example, the non-operational instruments 138 can include portions of instruments that can be attached to manipulator arms 114 like fully operational instruments, but need only be inserted in cannulas or apertures of the anatomical model 120. Thus a shaft and end effector can be removed from a dummy instrument, and/or dummy instruments can be hollow instruments with no mechanism, or other non-operational versions of instruments that provide a user the experience of setting up and using such instruments during a simulated medical procedure.

Figure 2:
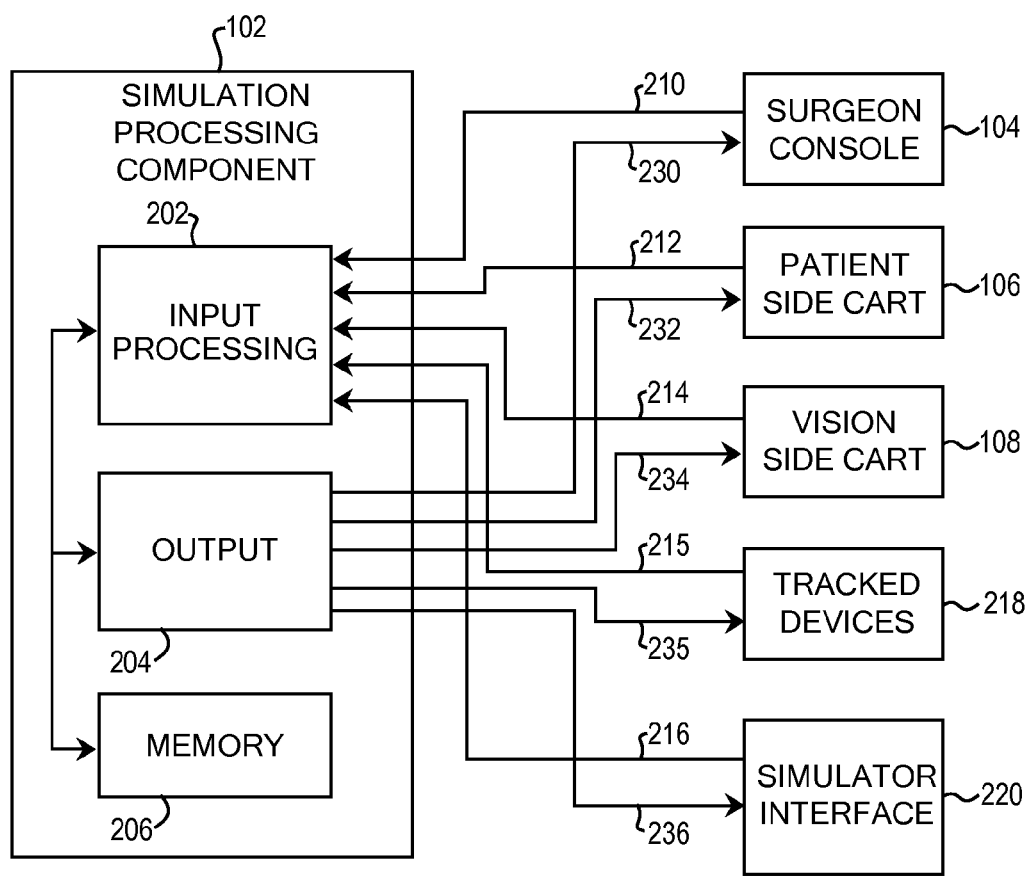
FIG. 2 is a block diagram illustrating an example of a simulation processing component and communication with other components of the simulation system.

FIG. 2 is a block diagram illustrating an example of a simulation processing component 102 and communication with other components of the simulation system 100.

Simulation processing component 102 can include an input processing block 202 which can perform various functions of the simulation. In some implementations, the input processing block 202 can implement one or more virtual environments for simulations provided by the simulation system. For example, the virtual environment can provide a two dimensional (2D) or three-dimensional (3D) environment that can simulate a physical surgical site or a portion thereof. In some examples, a portion of a human body can be simulated, including virtual models of skin surfaces and internal organs or other body structures, as well as virtual models of the surgical instruments and other objects used in an actual surgical operation. The virtual models can be changed and updated by the simulation processing block 202 based on signals 210 provided by the surgeon console 104 which indicate the manipulation of master controls on the surgeon console which direct how the surgical instruments on the teleoperated arms of the patient side cart are to be moved and manipulated. The signals 210 also can indicate other commands, such as entering particular usage modes, activating other surgical features (e.g., fluid spray, suction, etc.), or performing other functions.

Furthermore, the input processing block 202 can receive signals 212 from patient side cart 106. These signals can include the positions and orientations of the manipulator arms and surgical instruments of the patient side cart, as well as statuses of various controls on the cart 106 as described above. The input processing block 202 can also receive signals 214 from the vision side cart 108, which can include statuses of various controls on the cart 108, etc., as described above. The input processing block 202 can also receive signals 215 from tracked devices 218, which for example can include one or more sensors of the anatomical model 120 that track manually operated surgical instruments. Other components of the simulation system (not shown) can similarly provide signals to the input processing block 202, such as operating room sensors that track component positions, etc.

The input processing block 202 can also receive signals 216 from a simulator user interface (UI) 220 in some implementations. The simulator interface 220 can present one or more options or selections to user(s) of the simulation system 100 to customize and/or select features of the simulation of the medical procedure. The simulator interface 220 can be presented on one or more of the components of the simulation system, such as surgical console 104, patient side cart 106, and/or vision side cart 108. Alternatively, the simulator interface can be implemented on its own dedicated device, such as a computer system (desktop computer, laptop computer, server, portable device, etc.). For example, the simulator interface 220 can display options to a user, such as a number of different medical procedures to simulate, as well as various options, settings, and preferences for those medical procedures and for the components used in the simulation system. These selections can be provided in signals 216 to the input processing block 202. In some implementations, a single interface 220 can present options for simulated setup procedures as well as simulated surgical operations, thus allowing a unified interface to control simulated aspects of all stages of teleoperated medical procedures.

The simulation processing component 102 can also include an output block 204. This block can provide signals to control or drive various components of the simulation system 100, as instructed by the simulation processing block 202. For example, some signals can be signals to command functions on a component, such as signals controlling actuators on the patient side cart to move telemanipulator arms or to command another medical function (air suction, etc.). Some signals can be simulation state signals that cause an output to the user. For example, the output block 204 can send a signal 230 output to the surgeon console 104 that provides video output on a display of the surgeon console, such as data causing a display of a virtual surgical site and virtual surgical instruments at the site that move in correspondence with a user's manipulation of the controls of the surgeon console 104. Similarly, the output block 204 can send signal 232 to patient side cart 106, signal 234 to vision side cart, and signal 236 to simulator interface 220 to drive video displays on these components that are relevant to their functions. For example, patient side cart 106 and/or vision side cart 108 can display a graphical virtual environment showing the surgical site based on a position of one or more endoscope instruments or other imaging instruments. Other visual output can be provided as well, such as status messages. In some implementations, output block 204 can send signals 235 to track devices to provide statuses, updates, etc. Other types of output can also be caused by signals to components, such as audio and haptic output. Simulator interface 220 can display an interface that can update its visual appearance based on input received from a user as provided in signal 236, such as a graphical user interface displaying graphical menu items and/or other selections and options, or other type of interface.

Simulation processing component 102 can also include memory 206 in communication with the simulation processing block 202. Memory 206 can store various data needed by the simulation processing block 202 and simulation system 100. For example, program instructions for implementing simulations and data describing one or more virtual environments, three-dimensional models, and various settings can be stored in memory 206. In addition, in some implementations, the simulation processing component 102 can monitor parameters based on events and actions occurring during simulated procedures, and can store such parameters in memory 206. For example, parameters such as time taken to perform a task that the procedure, positions of components during procedures, etc. can be stored, as described below.

Figure 3:
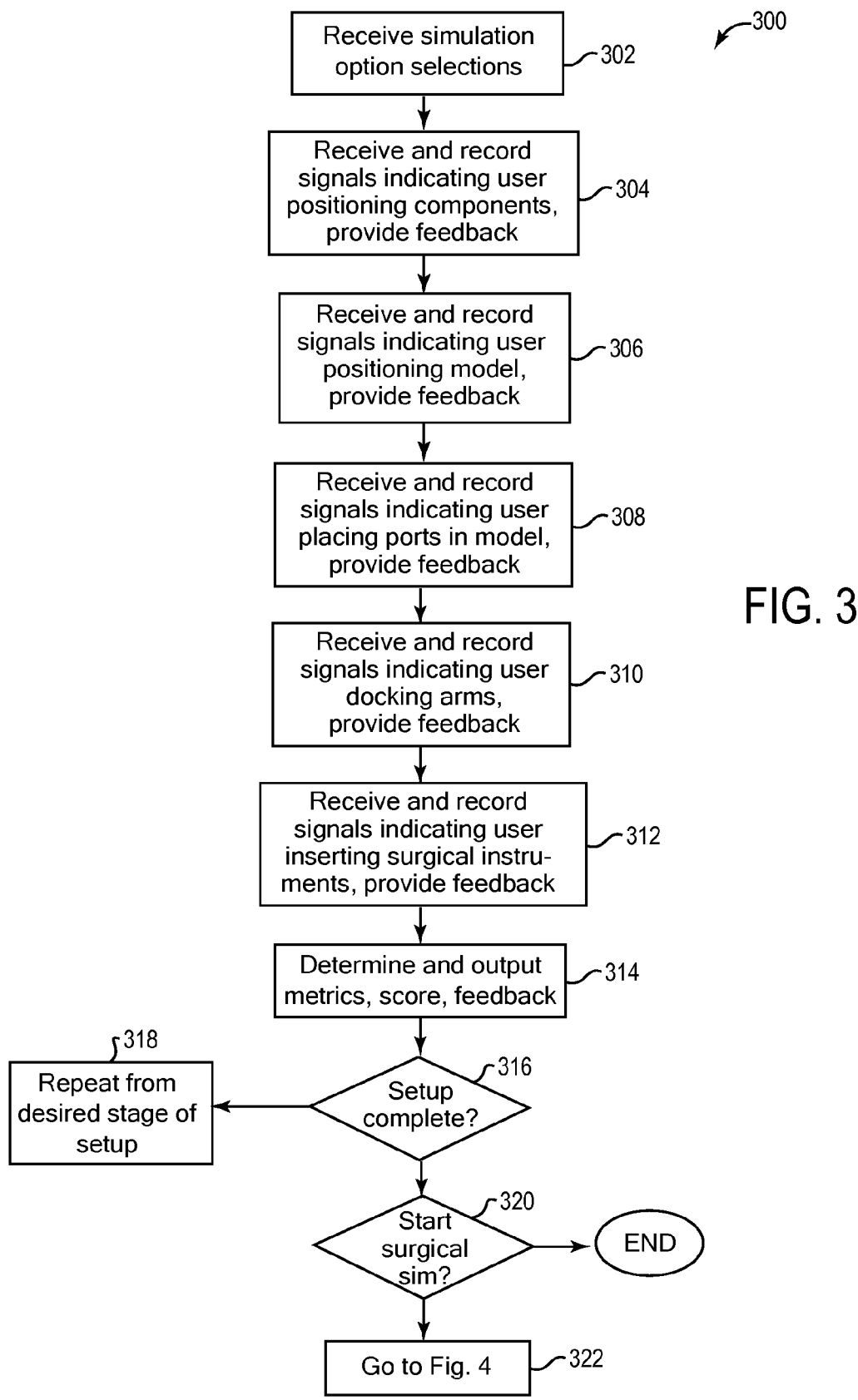
FIG. 3 is a flow diagram illustrating an example method for providing a simulated setup procedure according to one or more implementations described herein.

FIG. 3 is a flow diagram illustrating an example method 300 for providing a simulated medical procedure according to one or more implementations described herein. Method 300 can be controlled and/or coordinated by the simulation processing component 102. In this example, a simulated setup procedure is described for configuring one or more components of the simulation system before and in preparation for a simulated surgical operation that can be performed after the setup procedure. This example assumes the use of a patient side cart 106 having manipulator arms in the simulated setup procedure. Other implementations can include similar or equivalent setup components or tasks.

The simulated setup procedure of method 300 can be performed while one or more user trainees are forming the setup tasks. For example, a single trainee can be required to perform all the tasks to obtain comprehensive training. In other implementations, multiple trainees can be simultaneously or otherwise required to perform setup tasks for the simulated procedure as in an actual surgical procedure. For example, one trainee may be required to position components in operating room, anther trainee place ports, and another trainee position manipulator arms for docking. Advantages of the simulation system include the ability to train multiple trainees on a single system and or at the same time.

In block 302, the simulation processing component receives simulation option selections. These can be various selections to configure the setup procedure, and can be input by a user from a displayed interface, such as a graphical user interface 220 displayed by a display device of the surgeon console 104 and/or of vision side cart 108, for example. Selections can include the type of surgical operation that is to be set up for simulation, such as procedures designed for general, urologic, gynecologic, transoral, cardiac, thoracic, and/or pediatric surgical operations. Selections can also include the particular system components to be used in the setup procedure, the experience level of the user trainee(s) involved, a difficulty level of the simulation (novice, standard, expert, etc.), time parameters for the procedure, etc. In some implementations, this interface can be the same interface used for the simulated surgical operations performed after setup (e.g., as described in FIG. 4).

In block 304, the simulation processing component receives and records signals indicating that the user is positioning one or more components of the simulation system. Such components may be required to be positioned in particular locations in the simulation area, e.g., absolute positions in the area or positions relative to each other. For example, the patient side cart 106 can be placed relative to an operating table and/or anatomical model, and/or the vision side cart 108 can be positioned relative to the patient side cart 106, surgeon console 104, or other components. In some implementations, additional components can be positioned during setup simulation, such as the surgeon console and in any other components being used (anesthesia table, etc.). In some implementations, the component positions can be tracked using sensors, such as sensors for cameras positioned over the physical simulation area, sensors detecting the motion of the components, etc., and these positions can be sent to, monitored and recorded by the simulation processing component 102. A user can also indicate to the processing component that he or she has completed placing the components of the system, e.g., by providing input via the vision side cart 108 or other component. The simulation processing component 102 can record parameters such as the received signals and times taken to complete tasks, and can output signals causing feedback to be provided during this block. For example, feedback can include a visual and/or audio displaying of instructions as to placement, graphical spatial diagrams or maps of actual and/or desired component placement, alerts when the user has deviated too much from appropriate placement, warnings when specific measures are not taken (e.g., moving the patient side cart without placing the arms up), etc. Feedback can be displayed on one or more of the output devices of the system components, in some implementations.

In block 306, the method can receive signals indicating that the user is positioning a model for the setup procedure. For example, in some implementations static registration techniques can be used, where the user can move manipulator arms and instruments of the patient side cart 108 to touch the surface of the model at one or more known locations. Using the sensors tracking the position of the arms, the simulation processing component can determine the position and orientation of the model in 3-D space relative to the elements of the patient side cart, such as manipulator arms and/or surgical instruments. For example, this allows a virtual scene of the operating room and/or surgical site to be rendered and also can allows the simulator system to provide directed feedback, e.g., suggestions, evaluation and/or scoring, on which port(s) the user is currently using and how to move to the correct port, if appropriate. Other methods can be used in other implementations, such as using a laser alignment guide or docking an arm to a rigid fixture that constrains the position and orientation of the model. The user can indicate to the simulation processing component that he or she has completed positioning the model. In some implementations, the simulation processing component 102 can record parameters such as sensor signals and times taken to complete tasks, and can provide feedback on user progress of the tasks performed during this block, such as updating visual displays.

In other implementations, the positioning of the anatomical model can be sensed at a later time in method 300 instead of at block 306. For example, the position and orientation of the model relative to the teleoperated medical device can be sensed after docking in block 310 using sensors of the teleoperated arms, and/or using sensors of the model.

In block 308, the simulation processing component receives and records signals indicating that the user is selecting or placing ports at a physical surgical site for use in a surgical operation. For example, the ports can be placed in an anatomical model positioned at and/or including the physical surgical site. The ports are apertures or other locations in the model through which surgical instruments will be inserted, and the ports have specific pattern or distance requirements depending on the target anatomy and surgical operation selected for simulation. In some implementations, placing ports can include placing cannulas in selected apertures of the model (e.g., which can be detected from sensors in the model in some implementations), such as camera cannulas and operating instrument cannulas so that the desired surgical site portions are in view of an endoscopic or other camera surgical instrument and are in operating range of operating instruments to be placed in the cannulas. In some implementations, the system can detect the placement of ports using sensors within the anatomical model, and/or using sensors in the teleoperated arms after docking (described below). The user can indicate to the simulation processing component that he or she has completed placing the ports. The simulation processing component 102 can record parameters such as sensor signals and times taken to complete tasks, and can provide feedback on user progress or correctness of the tasks performed during this block (such as the correctness of position of placed ports), including updating visual displays.

In block 310, the simulation processing component receives and records signals indicating that the user is positioning ("docking") the manipulator arms and/or other elements of the patient side cart in appropriate positions and locations above or within selected ports of the model. For example, the user can position manipulator arms at particular angles, distances from each other, etc., in view of parameters such as mutual manipulator collision avoidance and required instrument range of motion. The simulation processing component receives signals from sensors in the arms of the patient side cart, which indicate the positions and orientations of the manipulator arms. Various implementations allow the user to manually move the arms or other elements by hand, and/or with remote control. The user can indicate to the simulation processing component that he or she has completed the docking. The simulation processing component 102 can record parameters such as sensor signals and times taken to complete tasks, and can provide feedback on user progress or correctness of the tasks performed during this block, such as updating visual displays.

In block 312, the simulation processing component receives and records signals indicating that a user is inserting the surgical instruments of the patient side cart in ports. The simulation processing component receives signals from sensors in the arms of the patient side cart and/or from sensors and surgical instruments which indicate the positions of the surgical instruments relative to the arms and/or surfaces of the model. Requirements can include particular distances or amounts of insertion, locking an instrument in place, etc. In some implementations, sensors in the model can detect instruments within cannulas.

In some implementations, the surgical instruments are dummy instruments that are not functional as surgical instruments. In addition, if manual (e.g., non-teleoperated) instruments are being used, sensors of the model (and/or at other locations in the operating room) can track positions of such manual instruments. A user can indicate to the system that placement of the surgical instruments is complete. In some implementations, the simulation processing component 102 can record parameters such as sensor signals and times taken to complete tasks during block 310. The processing component can also provide feedback in block 312. This can include the simulation processing component 102 outputting signals to cause a video display of various virtual images, progress indicators, suggestions, hints, warnings, etc. regarding instrument insertion by one or more display screens of the simulation system.

In blocks 304-312, various types of video output can be provided. For example, an assistant user can view the display (e.g., at a vision side cart 108) to assist in determining whether arms and/or surgical instruments are properly positioned during the setup procedure. A display of the surgical site can include the current positions of surgical instruments and other objects at the surgical site. In some implementations, the display shows captured images of the physical surgical site at the patient side cart and/or model, such as captured by an endoscope instrument or other imaging instrument of the patient side cart (e.g. ultrasound sensors, patient vital sign sensors, etc.), model cameras or sensors, and/or other visual sensors directed at the physical site. This setup can be used for training on inanimate/dry-lab models or live tissue models, such as porcine or cadaveric training protocols.

In other implementations, the display shows a virtual environment and virtual surgical site generated by the simulation processing component and based on detected positions of surgical instruments and/or other objects at the physical surgical site. For example, the surgical instrument positions can be known from sensors in their manipulator arms, and positions of other objects at the site can be known from captured images sent by camera(s). The simulation processing component generates the virtual environment based on these known images and positions. The virtual surgical instruments and objects can be displayed to appear similar to their physical counterparts (if any), or can be displayed as virtual objects with different appearances in the virtual environment.

In some implementations, the virtual environment can include display of realistic surroundings such as would be seen in an actual medical procedure. For example, the background of the displayed surgical site can include body walls, blood vessels, or other realistic surroundings. In some implementations, the virtual environment can include accurate representations of the physical objects at the site, while the background and surroundings of the site can be made to look realistic as an actual medical procedure (e.g., as shown in FIG. 8B).

In block 314, the simulation processing component can output feedback information such as final parameters, metrics, score, and/or other feedback related to the setup procedure. In some implementations, feedback information may also or alternatively be displayed to the trainee during the performance of or upon completion of one or more tasks or exercises (e.g., in blocks 304-312), so that the trainee can monitor his or her progress or can compare his or her performance against other persons from a novice to expert range.

For example, metrics can be determined from recorded parameters and can include the times expended by an assistant for various tasks during the setup procedure, as well as a summary of the placement positions of the components and instruments used in the setup. An evaluation and score can also be determined by the simulation processing component based on the tasks completed by the user during the setup procedure, as described in greater detail below. The simulation processing component can output feedback indicating the result of evaluation, such as how well the trainee performed tasks, as well as hints or instructions for performing the tasks better. Some or all of this information can be output on one or more displays or other output devices of the simulation system.

In block 316, the method checks whether the setup is complete. For example, the simulation processing component 102 can evaluate the resulting positioning of the system components and determine whether the system components and surgical instruments are adequately placed to allow a surgical operation to continue. If any placements are sufficiently incorrect, or the user requests to repeat a stage, then in block 318 the simulation processing component causes the user to repeat the appropriate stages or blocks of the setup procedure.

If the setup is complete, then in block 320, the method can check whether a simulated surgical operation should be started on the same simulation system used for the setup procedure. The surgical simulation may have been indicated in the simulation selections of block 302, for example. If a surgical operation simulation is to commence, the method continues as described in FIG. 4. Otherwise, the method ends, or various further actions may be taken to continue or repeat training, such as replacing a surgical task exercise at the physical surgical site of the anatomical model with a different exercise.

Figure 4:
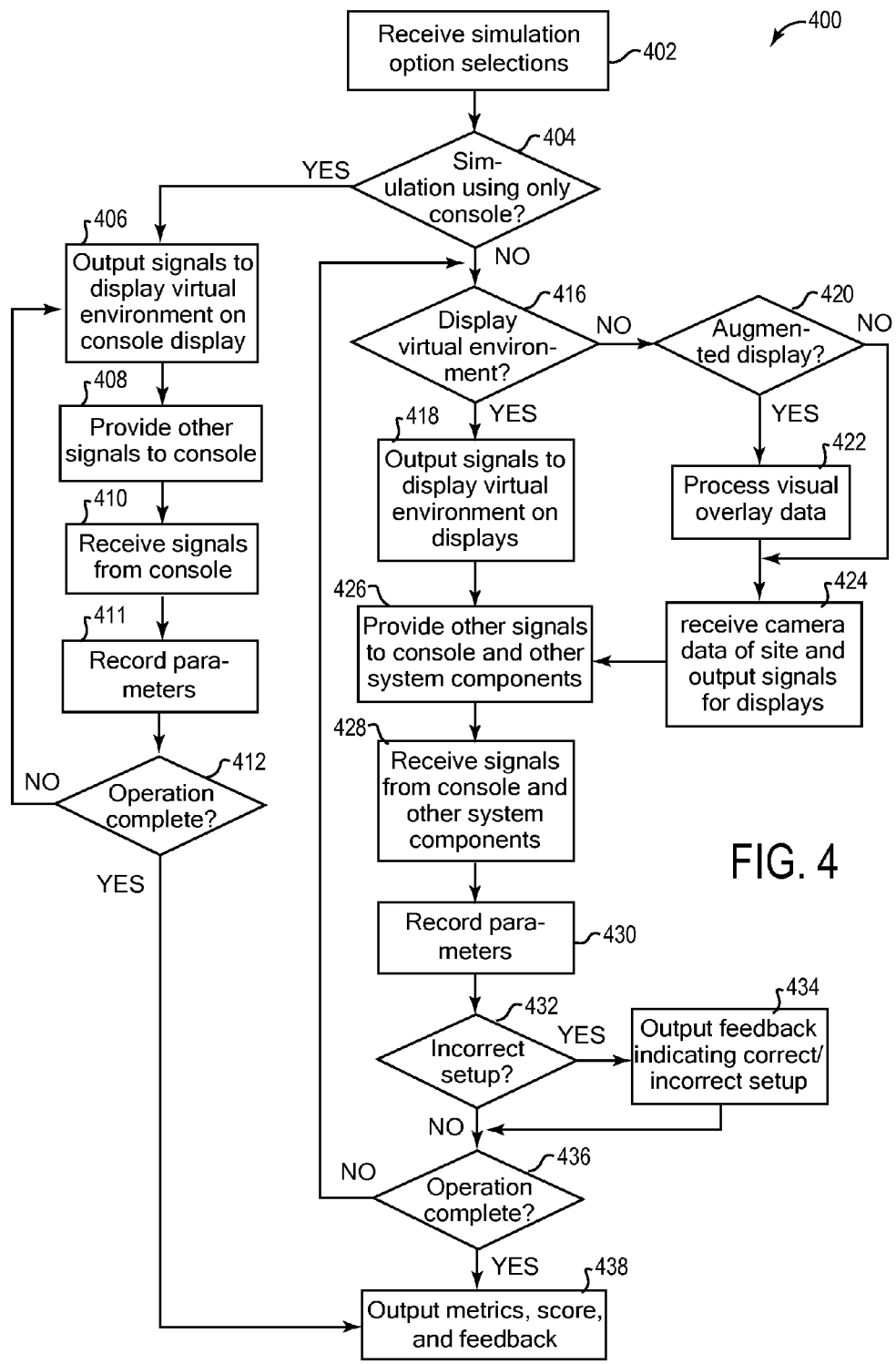
FIG. 4 is a flow diagram illustrating an example method for providing a simulated surgical operation according to one or more implementations described herein.

FIG. 4 is a flow diagram illustrating an example method 400 for providing a simulated surgical operation according to one or more implementations described herein. In this example, a simulated surgical operation is described for performing surgical tasks at a surgical site (virtual site and/or physical site). Method 400 can be controlled and coordinated by the simulation processing component 102.

In some implementations, method 400 can be performed after the setup procedure of FIG. 3. Thus, such implementations can offer the ability to use a simulation framework on a teleoperated medical system with a separate surgeon console and patient-side cart to monitor and track progress and to display output and feedback, all under a single software and user interface (UI) framework. Method 400 is described assuming the setup of the simulation system components has been completed as described in FIG. 3.

The simulated setup procedure of method 400 can be performed with one or more user trainees performing the surgical tasks. For example, a single trainee can be required to perform simulated surgical tasks using the surgeon console. In other implementations, multiple trainees can be simultaneously or otherwise required to perform surgical tasks for the simulated procedure as in an actual surgical procedure. For example, one (surgeon) trainee may be required to control instruments using the surgeon console, while a different (assistant) trainee may be required to control an additional manual instrument at the surgical site, or perform some other assistant function (e.g., exchange instruments, adjust positions of arms on patient side cart, adjust brightness of the endoscope feed, adjust ports, pass sutures to a teleoperated instrument using a manual laparoscopic instrument, coordinate a uterine manipulator to assist the console surgeon, etc.). Two (or more) surgeon trainees at two (or more) surgeon consoles can divide control of tasks, exchange control of instruments, and/or provide training to each other if, in other examples. Advantages of the simulation system include the ability to train multiple trainees on a single system and or at the same time.

In block 402, the simulation processing component can receive options and selections for the simulation. Such selections can include the type of surgical operation to be performed, particular stages or sub-stages of the operation to be performed, the particular components and/or instruments to be used, etc. For example, the same graphical interface used to provide selections to the setup procedure of FIG. 3 can be used for the surgical operation.

In block 404, the method checks whether the simulation is using only the surgeon console, without other components such as a patient-side cart and vision side cart. For example, the user may have designated a console-only simulation in block 402. If only the surgeon console is to be used, then in block 406, the simulation processing component 102 outputs signals (such as simulation state signals) to display a virtual environment on the console display device. This virtual environment can depict the surgical site at which the user of the console will be operating. For example, a 3-D virtual environment can be displayed, including virtual anatomical structures that appear similarly to corresponding real anatomical structures. In addition, virtual surgical instruments controlled by the user of the console are also displayed in the virtual environment. The particular virtual anatomical structures and virtual surgical instruments displayed in the virtual environment can be based on the selections made in block 402, where the simulation processing component can determine the appropriate environment based on the type of procedure selected and other selections made by the user.

In block 408, the simulation processing component provides other signals to the console. The signals can include simulation state signals such as audio data informing the user of any events or interactions occurring in the virtual environment, haptic data for outputting haptic output at the console, and/or any other applicable data. In some implementations, the provided signals can also include performance feedback information such as metric, score, instructions, alerts, hints, or other information.

In block 410, the simulation processing component 102 receives signals from the console. These signals can include directional or positioning signals based on user manipulation of controls on the console, such as hand grips, buttons, foot pedals, and other controls. The simulation processing component can update the virtual environment based on the signals received from the console, including moving virtual surgical instruments to correspond with the user input as if the user were controlling physical teleoperated surgical instruments. Simulation processing component 102 can also determine interactions of the virtual surgical instruments with virtual anatomical structures, e.g., according to a physics model.

In block 411, the simulation processing component records parameters such as signals and events communicated during the simulation procedure. For example, such signals and events can be signals sent and received in blocks 406-410, alerts or other performance feedback provided in these blocks, user input provided in these blocks, the times expended by trainee(s) to complete surgical tasks, etc.

In block 412, the simulation processing component can check whether the simulated surgical operation is complete. For example, the user can indicate that the simulation is over via input by console controls. If the operation is not complete, the method returns to block 408 to receive signals from the console and continue the simulation in the virtual environment. If the operation is complete, the method continues to block 438, described below.

If in block 404 the method finds that the simulated surgical operation is not only using a surgeon console, then the method continues to block 416, in which the method checks whether the simulation will display a virtual environment. For example, a virtual environment can be displayed on a console display and other displays of the simulation system, such as a display on the vision side cart, and can be a similar virtual environment as described above for block 406. If a virtual environment is to be displayed, then in block 418 the simulation processing component 102 outputs signals (such as simulation state signals) to one or more components to display the virtual environment on displays. The method then proceeds to block 416, detailed below.

If in block 416 the method determines that a non-virtual environment is to be displayed, then images of a physical surgical site as captured by a camera are to be received and displayed. In block 420, the method checks if an augmented display is to be output. An augmented display allows the display of computer-generated graphics over the images captured by a camera. If not, the process continues to block 424. If an augmented display is to be used, in block 422 the simulation processing component processes visual overlay data to be overlaid on received images. For example, such visual overlays can include text, graphics, and interface objects which provide feedback information such as alerts, instructions, etc. In some implementations, the visual overlays can provide indicators to instruct where arms, surgical instruments, or other components of the system should be positioned.

In block 424, the simulation processing component 102 receives camera data from one or more endoscopes and/or other imaging instruments (e.g., ultrasound sensors, vital signs sensors, etc.) providing images of the physical surgical site and/or simulated patient. For example, an endoscope can be one of the surgical instruments provided on an arm of the patient side cart. The simulation processing component 102 also determines and outputs signals (such as simulation state signals) to display the images of the surgical site on display devices of the system, such as display screens at the surgeon console 104 and the vision side cart 108 (if being used). If no augmented images are being used, the output signals include only the camera data. Otherwise, the augmented visual overlay signals of block 422 are combined with the camera images and the combined signals for output for display. Later in the simulation, the signals are used to update the displays.

In block 426, the simulation processing component 102 provides any other signals to the surgeon console and to other system components. The signals can include audio data for outputting audio at system components, haptic data for outputting haptic output at system components, etc. In some implementations these signals can include control signals received from the surgeon console which the simulation processing component relays to the patient side cart and/or vision side cart. Similarly, the signals can include position signals and/or control signals received from the patient side cart which the simulation processing component relays to the surgeon console and/or to the vision side cart. In some implementations, the provided signals can also include feedback information provided to system components, such as metrics, scores, instructions, alerts, hints, or other information (and/or feedback information can be included in augmented visual data in block 422).

In block 428, the simulation processing component 102 receives signals from the surgeon console 104 and other system components, such as the patient side cart 106 and the vision side cart 108 (if present). For example, control signals from the surgeon console can indicate the manipulations of controls on the console by the console user, such as master levers used to move and otherwise manipulate the arms and surgical instruments of the patient side cart 106. Signals from the patient side cart can include position signals from sensors in teleoperated arms and surgical instruments indicating the position and orientation of those arms and instruments. Signals from the vision side cart can include control signals from controls on that cart operated by an assistant user. In some implementations where manual surgical instruments are being used with an anatomical model, the simulation processing component can receive signals from the model, which can include sensor signals indicating positions of manual surgical instruments inserted in or contacting the model.

In block 430, the simulation processing component records parameters such as signals and events communicated during the simulation procedure. For example, such signals and events can be signals sent and received in blocks 418-428, alerts or other performance feedback provided in these blocks, user input provided in these blocks, the times expended by trainee(s) to complete surgical tasks, etc.

The blocks 406-410 or blocks 416-428 can be implemented during a performance of one or more surgical tasks and/or exercises of the simulated surgical operation. For example, a user such as a trainee surgeon can perform a simulated exercise at a simulated surgical site by teleoperating the surgical instruments inserted through the cannulas in the model, for by controlling virtual instruments. Such exercises can include suturing, manipulating objects, etc. at a virtual or physical surgical site, or one or more other simulated tasks. Assistant trainees can be performing patient-side tasks simultaneously or between tasks in some implementations.

In block 432, the simulation processing component checks whether an incorrect setup has been in place during the surgical operation simulation. This can be the case when a setup procedure was simulated before the surgical operation and included incorrect selection of model ports, positioning of system components (e.g., teleoperating arms, surgical instruments, or anatomical model), or included other incorrect settings or selections. Such incorrect setup settings can have a significant effect on a following surgical operation. For example, collisions may occur between arms or instruments, ranges of motion may be blocked, limits of motion may be prematurely reached, etc. If the simulated surgical operation was performed using this incorrect setup, then in block 434 the simulation processing component outputs feedback to the one or more users of the simulation indicating the incorrect setup and how and this incorrect setup has affected the surgical operation. For example, output feedback information can indicate that a mis-positioned arm or surgical instrument caused surgical tasks to be missed or performed poorly, unintended changes to be made to simulated patient tissue, etc. This feedback can also indicate the correct setup to allow the users to correct any errors. In some implementations, such feedback can be output at any point during the simulated surgical operation.

After block 434, or if the setup was correct, the method continues to block 436, in which the method checks whether the simulated surgical operation is complete. For example, this can be indicated by one or more users providing input to the system to indicate the operation is over, or the simulation processing component can automatically determine that the operation is over based on evaluating component positions, the images of the surgical site, etc. If the simulated operation is not complete, the method returns to block 416 to continue displaying the surgical site environment and communicate signals between system components. If the simulated operation is complete, then the method continues to block 438.

In block 438, the simulation processing component outputs feedback information such as final parameters, metrics, score, and/or other feedback to the users of the simulation. In some implementations, feedback information may also be displayed to trainee(s) during the performance of or upon completion of one or more exercises (e.g., in blocks 406-410 or 416-428), so that a trainee can monitor his or her progress or can compare his or her performance against a database of other persons from a novice to expert skill levels. Similarly as described above for the setup procedure of FIG. 3, metrics can be determined from parameters and can include the times taken by the users for various tasks during the surgical operation, a summary of the placement positions of the components and instruments used in the surgical operation, etc. An evaluation and/or score can also be determined by the simulation processing component based on the surgical tasks completed by the user during the surgical operation, as described below. The simulation processing component can output feedback indicating the result of evaluation, such as how well the trainee performed tasks, as well as hints or instructions for performing the tasks better. Some or all of this information can be output on one or more displays and/or other output devices of the simulation system.

Evaluation and Guidance of Trainee Performance During Simulations

During the simulated setup procedures and surgical operations described above with respect to FIGS. 3 and 4, various data and parameters associated with the setup and surgical tasks can be monitored (measured) and recorded by the simulation processing component, such as the positions and motions of components at different stages of the various procedures, the times to complete various tasks, and so on. The system can determine metrics and perform an automatic evaluation associated with one or more trainees' performances during the simulation based on recorded parameters. The system can also provide real-time performance feedback to trainees during the procedure and based on evaluations, in order to provide guidance during the procedure and for later procedures.

In some implementations, an evaluation can include automatically comparing the parameters recorded during these procedures (and metrics determined therefrom) to stored reference parameters and metrics for the corresponding tasks. The reference parameters can be correct or optimal parameters for these tasks or parameters previously-recorded during previous simulated medical procedures. Parameters associated with relevant skills may be evaluated to measure trainee improvement or to compare one trainee's performance parameters to corresponding parameters demonstrated by other trainees (concurrent or historic) or by persons considered to have expert skill levels. Thus a trainee's skill level in a particular parameter may be evaluated relative to peers (e.g., to determine the trainee's progress with reference to anticipated improvement) or relative to experts (e.g., to identify deviations from a high skill level). Both patient-side skills of FIGS. 3 and 4 (associated with actions physically near the patient's location, e.g., manipulator arm position and orientation setup, cannula port placement, docking, assisting during surgical tasks, and the like) and surgeon-side skills (associated with performing surgical tasks in the surgical operation of FIG. 4, e.g., teleoperating or manually positioning an endoscopic camera and moving tissue instruments at the surgical site) can be evaluated.

An evaluation component can measure parameters associated with the tasks performed by a trainee, such as the overall completion time of all tasks, completion time of particular tasks, the position and orientation of manipulators or instruments, as well as other parameters of the actions taken by the trainee. In some cases, an evaluation can include determining one or more scores based on predetermined criteria associated with the parameters and the comparisons, where scores can indicate a performance level or skill of the trainee based on the performance in associated tasks. For example, a score can be based on the time needed to perform one or more tasks during the procedure and/or positioning or movement of system components during the one or more tasks. A trainee skill level associated with a specified parameter can be automatically scored by using kinematic and/or other sensor information obtained from a teleoperated medical system, such as from sensors of manipulator arms and of surgical instruments.

For simulated setup procedures such as in FIG. 3, an evaluation system may use sensor information to determine positions and orientations of instruments directed during an exercise. For example, the sensor information can include kinematic information from the manipulator arms obtained during the performance of blocks 304-310 (e.g., using remote center positions of the surgical instruments and setup joint values), as well as sensor information from other sensors used in the procedure. In some implementations, a kinematic setup template can be created that defines a specific effective or ideal manipulator position and orientation for a specific surgical task. Data associated with a trainee's surgical task exercise performance is compared against the template to create a performance score. This comparison can be used to determine if a trainee has properly selected ports for a specific surgical task exercise, if manipulator arm setup joints and other structures are properly configured to place the associated manipulator arms at a proper position and orientation, if cannula ports are properly positioned and spaced to allow effective surgical site access with minimized manipulator collision avoidance, etc. The ideal template information can be, for example, clustered or averaged positions, movements, and/or placements from prior performances of trainees and/or experts, or known optimal positions for instruments, arm components, etc.

In another example, a task exercise time parameter may be measured by starting a timer at the beginning of a cannula docking exercise and stopping the timer when the system senses that all manipulators have been properly docked to an associated cannula. As another example, a task exercise manipulator collision avoidance parameter may be measured by comparing sensor information from each docked manipulator arm against template sensor information to determine how close a trainee has come to placing the manipulators in prescribed ideal positions and orientations or within prescribed position and orientation envelopes. Similarly, sensor information from the manipulator arms, in conjunction with known physical dimensions of an anatomical model 120 can be used to determine if a trainee has properly positioned the cannulas in a correct port placement pattern in the model, or if the remote center of motion for each cannula (the location on each cannula that stays stationary in space as the manipulator arm moves) is correctly positioned so as to minimize tissue trauma at a patient's body wall.

Scores can be determined in a variety of ways. A trainee may be scored, for example, on how well port placement is selected for a selected surgical operation, or how long it takes to determine the correct port placement. Or, a trainee may be scored on how the manipulator arms are coupled to the placed cannulas (concerning, for example, manipulator arm collision avoidance) or how long it takes a trainee to couple the manipulator arms to cannulas placed in an anatomical model.

Metrics also may be sampled and/or determined to indicate a trainee's performance as he or she completes the exercise, and these intermediate evaluations may be plotted against a template to obtain a score. For example, historic data may indicate that specific acts should be completed in a certain order in order to most effectively complete a task, sensor data may be used to show the actual order in which a trainee performed the acts, and differences between the recommended versus actual order of acts completed is used to determine a trainee's score.

For surgical tasks performed during the surgical operation of FIG. 4, the system can similarly record and determine parameters such as completion time of one or more tasks of the exercise and arm positions based on kinematic data for computing metrics (e.g., movement volume, errors in the exercise, economy of motion of the instruments, etc.). Performance parameters can be measured at multiple times during the performance of surgical tasks during exercises and metrics determined from those parameters. In one example of a dry-lab exercise, a training exercise can require that the trainee pick up a ring with an operating instrument, move the ring along the pathway to a finish position (transferring the ring to another instrument controlled by a different hand as needed) without dropping the ring, while moving the camera to keep the ring and instrument tips in the center of view at all times, and while repositioning controllers to keep the trainee's hands in central controlling positions. In another example of a suturing exercise, the trainee can be required to drive a needle in a predetermined pathway of suture holes in the component while keeping the site in view of the camera, or suture an opening closed with spatial requirements as to the locations of the sutures. Patient-side tasks during a surgical operation (e.g., an assistant trainee guiding one or more instruments at the surgical site, controlling accessory equipment, etc.) can have their performance similarly measured.

Scores and/or other results of the surgical operation evaluation indicate an estimated level or skill of the trainee for the evaluated surgical exercise. Some implementations can provide graphical feedback, e.g., indicating how close the operating instrument end effectors are to ideal or correct positions for the surgical task, and/or ideal locations for sutures, cuts of tissue, etc. Some implementations can output real-time feedback during the task performance, such as indicators of correct or incorrect sutures, instrument positions, hints to the trainee, etc. Some real-time feedback can be instructional, indicating how instruments should be placed, moved, or positioned.

In some examples, parameters and/or scores can be determined a first time based on a particular user's or team's performance, and the same parameters and/or scores can then be recorded at a second time during the performance of the same type of procedure. These parameters can then be compared to evaluate the same user's or team's performance for particular procedure. In other examples, the parameters can be recorded for different users or teams, and compared to evaluate and compare the different users and teams.

Such scoring of a trainee based on simulation procedures allows performance and improvement of that trainee to be measured. In addition, a trainee can be scored in relation to other trainees or in relation to historic data in order to determine how well the trainee can perform the required task and/or to evaluate the trainee's relative learning speed and effectiveness and/or determine the trainee's skill level. Also, aggregate historical scoring may reveal that trainees have difficulty performing a certain task, and so training can be modified to improve a training program for that task.

The methods of FIGS. 3 and 4 can also be used to measure and evaluate performances of multiple trainees or teams at once and in various roles during a training exercise. For example, the simulation system can provide training for teams of persons, such as one or more surgeons, assistants, nurses, etc. In some examples, one or more assistant trainees can perform patient-side tasks for the methods of FIG. 3 and or FIG. 4, and a surgeon trainee can perform surgical tasks in the method of FIG. 4 while operating a console. Trainees other than the surgeon can use an anatomical model to practice patient-side skills (e.g., port placement, docking, system setup, camera and instrument insertion) since they will often perform these activities in the operating room. The team can also train their communication to perform and coordinate various tasks such as exchange instruments, adjust ports, pass sutures using a conventional laparoscopic tool, coordinate a uterine manipulator to assist the console surgeon, etc.

In some implementations providing training for such teams of trainees, the evaluation and scoring methodology described above can be extended to evaluate the performance of operating room teams in addition to individual trainees. For example, various scores can be output indicating the performance level or skill for coordinated team tasks. Such evaluation can be assisted by automated metrics to track progress and compare to historical data similarly as described above. These features can help provide proficiency standards for teams to understand their efficiency and how they can improve.

Some examples of teleoperated medical procedure training, evaluation and scoring are described in co-pending U.S. patent application Ser. No. 13/968,253, entitled, "Anatomical Model and Method for Surgical Training," which is incorporated herein by reference in its entirety.

Figure 5:
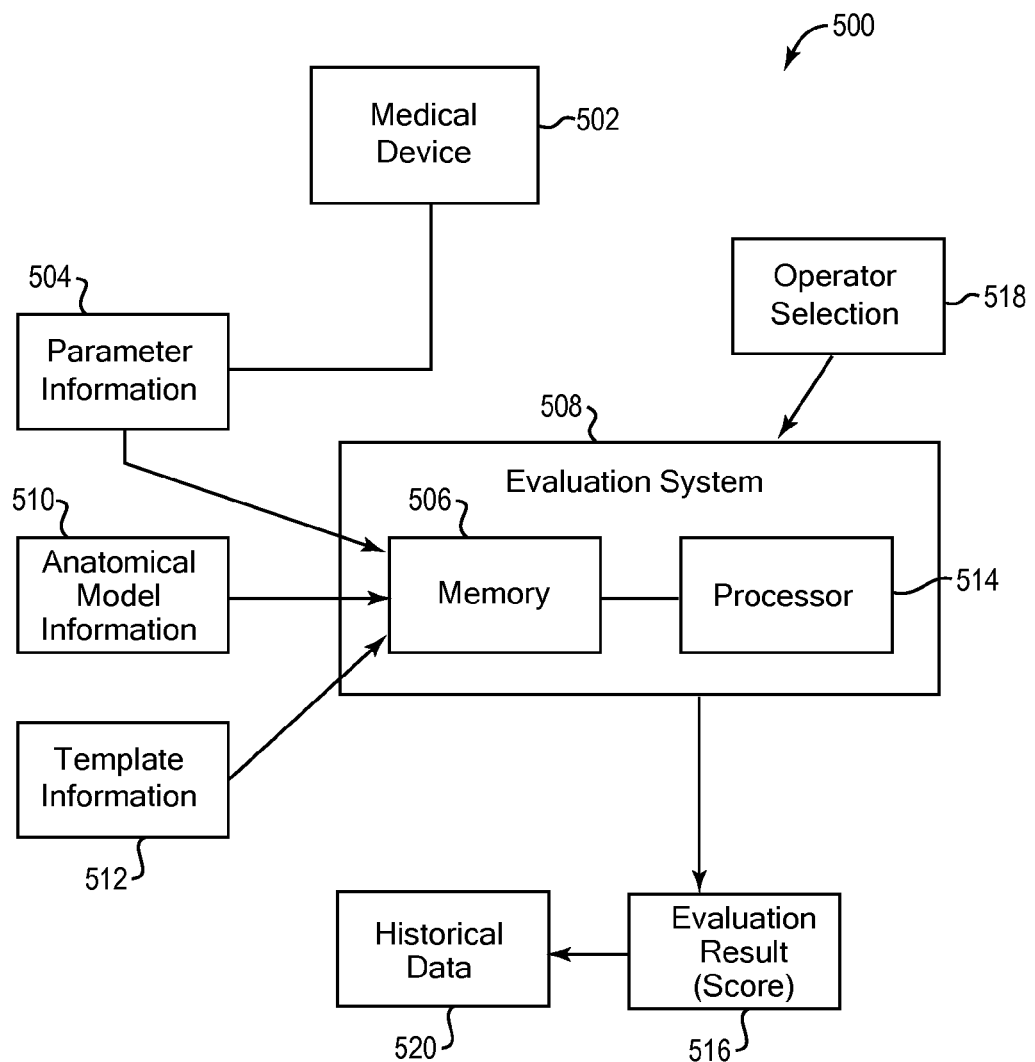
FIG. 5 is a diagrammatic illustration of aspects of an example system which can be used for automated evaluation of simulated medical procedures.

FIG. 5 is a diagrammatic illustration of aspects of an example system 500 which can be used for automated evaluation of simulated medical procedures using simulation system 100. As shown in FIG. 5, a medical device 502 is used, which in this example can include an input device such as a surgeon console 104, and/or a teleoperated medical device such as patient side cart 106, or other system that is capable of providing data concerning the position and/or orientation of one or more medical Instruments. The medical device 502 provides parameter information 504 to be stored in a memory 506 that is included in an evaluation system 508. For example, evaluation system 508 can be implemented in the simulation processing component 102 and memory 506 can be implemented in memory 206, for example.

Parameter information 504 can include performance parameters for a trainee's performance and/or related data, such as kinematic information or other sensor information as described above. Information 504 may be provided, for example, via an application program interface (API) interface in the simulation system. Parameter information 504 can be provided from a patient-side cart 106, and/or from other components of the system, such as information describing position and/or orientation of controls for a operator (such as a surgeon or trainee) on a surgeon console 104, vision side cart 108, etc.

In some implementations, anatomical model information 510 (e.g., physical dimensions, locations of possible cannula ports, location of surgical manipulators or instruments, etc.) associated with an anatomical model 120 is also input to the memory 506. Template information 512 can also be input into memory 506, indicating baseline, desired, and/or correct parameters and data for comparison to trainee performance parameters. Other parameter information can also be stored in memory 506, such as event data, e.g., recorded times related to trainee tasks and task completions, etc., and which can be collected and/or determined by other components of system 100 or 500 such as processor 514, sensors of the system, etc. Thus, memory 506 can be one or more physical memory locations that can store information that evaluation system 508 uses to carry out an evaluation of a trainee's performance. Such an evaluation is executed by processor 514, which can be one or more information processing devices (e.g., microprocessor(s) or other processing circuitry) that can be used to carry out the evaluation.

The evaluation results, such as one or more scores, guidance feedback, and/or other information, can be output via an output device 516, such as a visible display on a display screen or other display device, a physical printout from a printer, or other output. The individual exercise results may be added to historic data 520 (e.g., depending on an input at operator selection input 518), which in turn may be used to modify template information 512. In some embodiments, an operator input device 518 enables a training system operator to input various selections related to training exercises, such as identifying a particular surgical exercise task to be carried out, and/or identifying a particular anatomical model that is being used. The evaluation system can automatically select the appropriate information (e.g., proper template information 512) to use to carry out the evaluation.

Embodiments of a evaluation system 508 may be embedded in teleoperated medical systems (e.g., with outputs displayed via the system's displays) or may be implemented, for example, on a separate small computer system, such as a laptop computer or other electronic device. Such evaluation systems may also be networked to a central database to facilitate data collection from a number of medical devices and from a population of medical personnel (e.g., surgeons) and to facilitate data and/or scoring comparison within the trainee or surgeon population.

In addition to use for surgical system training, various features disclosed herein may be used for tasks based on using manual surgical instruments in the simulated medical procedures. Scoring aspects for training can be adapted for training in such manual tasks, such as ability to reach locations at the surgical site, instrument interference, camera position, surgeon comfort, etc. Automated scoring aspects can be based on sensing a position of one or more components, such as cannulas, surgical instruments, etc. by various sensors in an anatomical model and/or in other locations as described above.

Various implementations can provide results of evaluations and/or guidance feedback to trainees' during and after the simulated procedures, indicating differences to ideal or desired positions, times, metrics and/or scores, trainee level and/or skill, and suggestions and/or instructions for the correct or desired results. For example, graphical diagrams can be displayed on a display device indicating how close the manipulator arms are positioned to ideal or correct positions for the surgical task. Furthermore, some implementations can output real-time feedback during the performance of tasks, such as indicators of correct or incorrect placements and positions of surgical instruments, hints to the trainee, graphical indications of correct positioning and orientation and the acceptable range of motions and placements for particular instruments, etc. Some real-time feedback can be instructional, indicating where and when in the procedure that instruments should be placed or positioned. The system can provide tutorials to persons, demonstrating how to select ports in a model, position components, and dock manipulator arms.

Figure 6A:
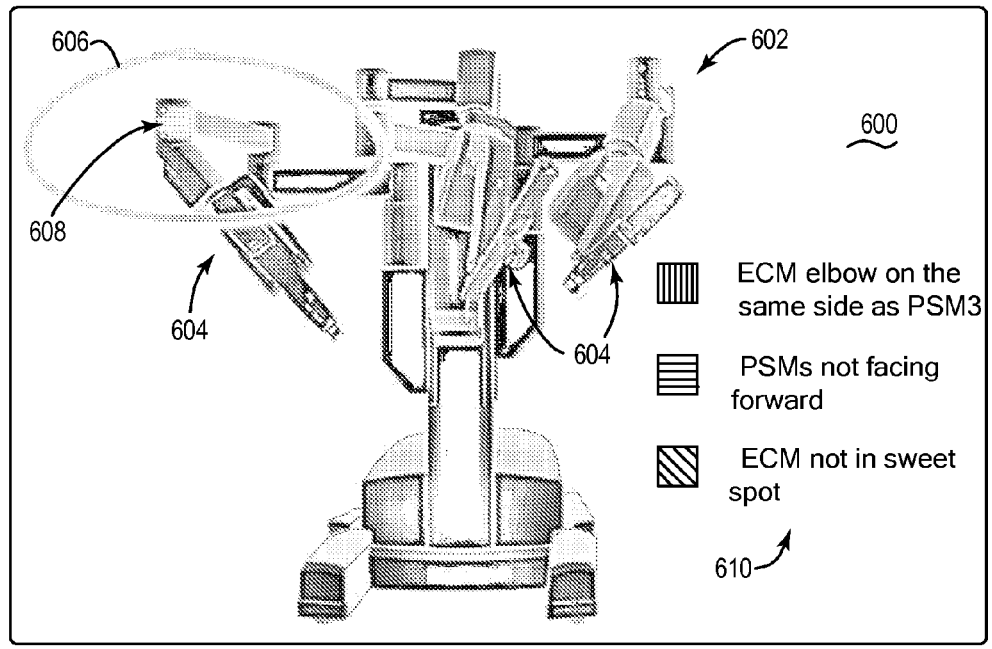
FIGS. 6A and 6B are examples of training image screens which can be displayed on one or more display screens of a simulation system.
Figure 6B:
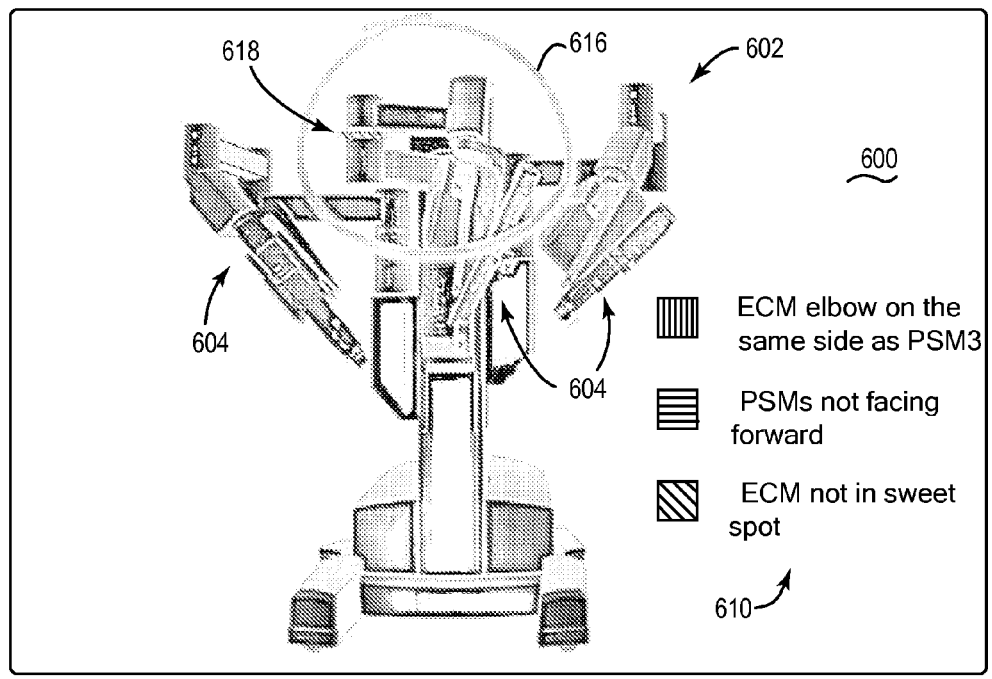

FIGS. 6A and 6B are examples of training image screens 600 which can be displayed on one or more display screens of a simulation system as described above. For example, the images on screen 600 can be displayed to assist and guide the user in placing the manipulator arms of the patient side cart during a setup procedure.

In FIG. 6A, display screen 600 shows an image 602 of an example implementation of a patient side cart, e.g., similar to a patient side cart 706 of FIG. 7A below. The image 602 includes images of three manipulator arms 604. In some implementations, during a setup simulation procedure, a user physically moves the physical arms corresponding to the arm images 604, where this motion is sensed by the simulation processing component (or other processing component) via arm sensors, and processing component causes the arm images 604 displayed on screen 600 to move in correspondence with the physical arms.

Indications can also be displayed to indicate the status of the arms relative to desired positions in a particular stage or block of a setup procedure. For example, the image 602 can indicate that the position of one or more of the arms of the physical side cart is currently incorrect or suboptimal. In one example, display screen 600 can display an enclosed line or border 606 around an area of the image 602 that is incorrect in position. In this example, the left manipulator arm 604 is shown to be incorrect in an area of its joints which are circled by the line 606. The line 606 thus directs the viewer's attention to the incorrectly positioned area. In some implementations, a more precise indication such as a highlight 608 of a particular joint can specifically point out the incorrect positioning. For example, the highlight 608 can be of a particular color, pattern, or other distinguishing mark. A legend 610 can indicate that particular problem that indicated by highlight 608, which in this case is that the left manipulator arm (Patient Side Manipulator, PSM) 604 is not facing forward enough, e.g., toward an anatomical model. Additional explanations of the incorrect positioning can be displayed in some implementations, if desired by the user.

FIG. 6B shows another example of display screen 600, in which a different portion of the physical patient side cart is incorrectly positioned as indicated in the displayed image 602 of the patient side cart. A line 616 indicates an area of the image 602 having inaccurate positioning, which in this example is an endoscopic center arm (ECM), i.e., the center arm 604 of the patient side cart. A highlight 618 indicates the particular joint of the arm 604 which should be corrected. For example, legend 610 informs the viewer that highlight 618 indicates that the center endoscopic manipulator 604 is not positioned in a "sweet spot" which allows the instrument of that harm to provide accurate or optimal views when inserted in a patient or model for the currently selected surgical operation. Other types of lines, borders, and/or indicators can be displayed in other implementations, including visual, audio, haptic, or other forms.

Virtual reality or other generated images such as those of screen 600, and/or augmented reality (AR) ghost images overlaid on camera images, can be displayed on system display devices to indicate or highlight system areas of concern or interest to users. For example, manipulator arm setup joints can have incorrect positions highlighted, as described above. In addition, reachability limits of manipulator arms and/or instruments can be displayed. Furthermore, spatial areas where internal or external collisions between arms and/or instruments can be highlighted as zones for the user to be aware of.

In some implementations, feedback information such as suggestions can be displayed on screen 600. For example, text suggestions can indicate an estimated amount of movement which would cause a highlighted arm to the mood into a correct position. Graphical suggestions can display correct positions (e.g., in a different color or other format) on the same display 600 relative to the current, incorrect positions. Broader hints can also be provided to allow the user to exercise judgment or make decisions. Such suggestions can guide the user in a training exercise to learn the correct way to perform tasks.

A variety of other types of feedback information can also be displayed on one or more display screens during setup procedures and surgical operations to provide guidance on system setup and accurate positioning of the manipulator arms, as well as guidance on surgical tasks. For example, text information messages such as instructions and alerts can be displayed to inform users of correct or incorrect actions or positioning during procedures. Some feedback can be provided in other forms, such as audio output or haptic output (e.g., on motor-controlled manipulator arms and/or surgical instruments).

The simulation system can thus provide guidance and feedback to trainees for system setup and skills during procedures such as dry-lab or wet-lab patient-side training scenarios. This can also reduce the burden on training assistants to constantly catch mistakes during simulation procedures, especially when training multiple trainees simultaneously. The system can also provide guidance and feedback during surgical operations and tasks, e.g., to assistant users operating the patient side cart (and other components) and/or manual instruments at an anatomical model, as well as the surgeon trainee operating the surgeon console.

Example Implementations

Many different variations of simulated surgical procedures can be implemented based on the simulation system 100 and methods described herein. Some example simulation configurations are described below.

The simulation can include a setup procedure using the patient side cart 106, vision side cart 108, and/or any other system components needed for simulating a setup for a surgical operation.

In some implementations, only the patient side cart 106 is used in the setup simulation. For example, a user can set up the position of the cart, the arms of the cart, and the surgical instruments of the cart, and the simulation processing component 102 can read the positions of these elements and provide current simulation state and feedback as to how well the setup was performed. For example, an output device such as a display screen on the patient side cart or on another component, and/or audio speakers, can be used to output representations of the current states of the setup procedure and/or feedback regarding user performance of the setup procedure.

Some implementations of the simulated setup procedure can include the use of an anatomical model. An assistant trainee can set up an anatomical model on an operating table. The model can be an inanimate model made of a rigid material and can be approximately shaped like a portion of a human patient. This model can be set up with a particular configuration for a particular surgical operation. For example, in inanimate training exercises, exercise devices can be placed within the model, such as beads or rings to be manipulated on wires, rubber or foam pieces of material to be sutured, cut, or otherwise manipulated with surgical instruments. In wet lab exercises, the model can be a biological specimen such as a porcine or cadaveric model, and/or one or more biological specimens can be placed within an inanimate model.

In some implementations of the setup procedure, the assistant trainee can position a patient side cart in an operating position next to the anatomical model. In some implementations, the simulation processing component 102 can receive signals indicating the position of the patient side cart 106 and the simulation processing component can provide signals to a display such as a display screen on the patient side cart 106 or vision side cart 108 which provide indications of the current states of the procedure and feedback to the assistant trainee as to the correctness of the positioning of the patient side cart relative to the anatomical model. In some implementations, the assistant can position the arms of the patient side cart to contact the model surface at multiple points on the surface, which locates the model relative to the patient side cart. The assistant trainee can then position the arms and instruments of the patient side cart relative to the anatomical model. The assistant can select appropriate apertures in the model, place cannulas into the selected apertures of the model, and then place the surgical instruments into the appropriate cannulas.

In some simulations, fully functional surgical instruments are provided on the arms of the patient side cart, and the trainee can insert the surgical instruments in ports on the model. In other implementations, one or more dummy instruments are provided on the arms of the patient side cart. These dummy instruments can include base portions of instruments which can be inserted into cannulas, but do not include end effectors such as claws, scissors, or scalpels.

In some implementations, manual instruments can also be used in the medical procedure in connection with the anatomical model. The assistant trainee can place manual instruments in appropriate apertures of the model and the positions of these instruments are tracked by the simulation processing component.

In various implementations, a vision side cart 108 can also or alternatively be used in the setup simulation. In some implementations, the vision side cart is used with an anatomical model and a patient side cart in the setup procedure. The user can view a model and/or the arms and instruments of a teleoperated medical device on a display screen of the vision side cart as captured by one or more cameras, e.g., positioned over and/or within the model. For example, the user can view a display screen of the vision side cart to determine if surgical instruments have been correctly positioned, based on the view of an endoscope which provides images of the surgical site to the display screen after the user has positioned the endoscope instrument. In some implementations, a virtual environment can be displayed that models the anatomical model, physical surgical site, and/or teleoperated arms and instruments. In some implementations, the user can be required to use controls on the vision side cart to control one or more functions in the simulated procedure.

In another implementation, the vision side cart is used in the setup procedure without the anatomical model and/or without the patient's side cart. For example, a user can be tested in positioning of vision side cart within the operating area, and/or the positioning of the vision side cart relative to other components such as a surgeon console.

In some implementations, one or more surgeon consoles can be included in a simulated setup procedure. For example, the positioning of the surgeon console within the operating area can be simulated. A surgeon trainee can also be required to perform some tasks during the setup procedure, such as port selection on an anatomical model. The surgeon console can be used singly, or in conjunction with other components, such as a patient side cart, vision side cart, and/or anatomical model. For example, a setup procedure can include only the surgeon console and an anatomical model, where the positioning of the components in the operating area, and the setup of instruments on the anatomical model are simulated. In one example, a virtual surgical site based on the physical side of the model can be displayed by the surgeon console while a user sets up manual instruments in the model.

Any other components of the simulation system can also be used singly or in conjunction with other components in a setup simulation. For example, the simulation processing component can monitor the used system components and the assistant can be required to position each system component correctly within an operating area or room.

In some implementations, the setup procedure can be the only simulation performed. In other implementations, a simulation of a surgical operation can be performed after the setup procedure, as in an actual surgical procedure. Alternatively, a simulated surgical operation can be performed on its own, without a simulation of a setup procedure.

The simulation of the surgical operation can be performed using a variety of implementations. In one implementation, only the surgeon console is used and the simulation component provides a virtual environment simulation in which virtual surgical instruments are displayed manipulating virtual structures at a virtual surgical site based on user input provided by the surgeon trainee operating the console.

In other implementations, only the surgeon console(s) and the anatomical model are used in the simulated surgical operation. For example, the teleoperated surgical instruments can be virtual instruments displayed in a virtual environment by the simulation processing component 102 and controlled by the console trainee. One or more real manual instruments can be inserted in the model and controlled by an assistant trainee, where the manual instrument position is tracked by the simulation processing component using sensors of the model, allowing the simulation processing component to display a virtual version of the manual instrument tip, or the image-captured manual instrument, within the virtual environment alongside the virtual teleoperated surgical instruments.

In another variation, the surgeon console and the patient side cart 106 are used in the surgical operation. In some examples, a virtual environment is displayed by the simulation processing component 102, e.g., on a display of the surgeon console 104. The trainee operating the surgeon console provides input controlling the physical arms and surgical instruments of the patient side cart, however, the simulation processing component displays corresponding virtual versions of these instruments at the surgical site on the displays of the simulation system. Thus, real or dummy instruments can be used for the surgical instruments of the patient side cart. One example of such an implementation is shown below with respect to FIGS. 7A and 7B.

In another variation, the surgeon console and patient side cart are used in a simulated surgical operation in which the physical surgical site is displayed on a display device of the surgeon console. For example, real, fully functional surgical instruments are inserted in the physical model, including one or more endoscopes having cameras which capture images of the physical surgical site (or other imaging instruments). The images are displayed on the console display. The console user thus sees the actual instruments he or she is manipulating. The simulation system can coordinate the simulation, including record parameters, provide guidance and evaluations, etc. One example of such an implementation is shown below with respect to FIGS. 9A and 9B.

In other variations, images displayed to users can be combinations of generated virtual graphics and captured images of a physical surgical site. For example, generated virtual instruments can be displayed alongside captured images of other, physical instruments, or images of physical instruments can be displayed alongside a virtual background generated to look like an actual surgical site. In some implementations, images of the physical surgical site can be combined with augmented images that are displayed over portions of the images of the physical surgical site. For example, graphics can be overlaid on the image of the physical site to provide feedback information such as statuses, instructions, alerts, and other information before, during, and after the medical procedure.

In other variations, a vision side cart is included in the system. Any of the above displays of the surgical site can also be displayed on one or more displays on the vision side cart that is viewed by an assistant user. In some implementations, the surgeon console and vision side cart can display different images or views in some implementations. For example, some display screens of the simulation system can display an endoscopic or camera view of the physical surgical site, while other display screens of the system can display a virtual environment that corresponds to the physical surgical site. For example, a camera view of the physical site can be displayed by the vision side cart for the assistant user to operate manual instruments at the site. Meanwhile, a virtual environment corresponding to the physical site can be displayed on the surgeon console. In another example, the vision side cart can display instructional feedback instead of or in addition to images of the surgical site displayed by the surgeon console.

Figure 7A:
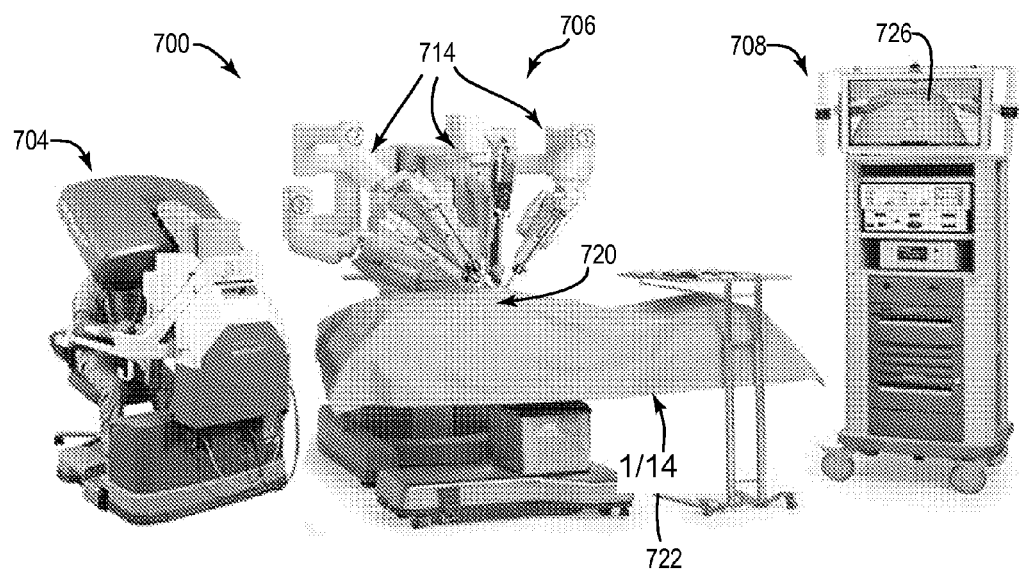
FIG. 7A shows one example simulation system including examples of several components described herein.

FIG. 7A shows one example of a simulation system 700 including examples of several components described herein. A surgeon console 704 can provide controls for a user such as a surgeon or surgeon trainee, who sits at the console to manipulate the controls, and can also include the display screen (shown in FIG. 5B). A patient side cart 706 includes a number of manipulator arms 714 which include surgical instruments at the ends of the arms and which are responsive to the controls operated by the user at the surgeon console 504. An operating room table 722 is positioned adjacent to the patient side cart 706, and can include an anatomical model 720 which can receive the surgical instruments of the patient side cart (the model in this example is covered by the cloth over the operating table). A vision side cart 708 can include a display screen 726 and other components, such as electronic equipment. In this example, the display screen 726 displays a virtual surgical site generated by the simulation processing component. For example, the model 720 can be only a surface or object having one or more apertures and not having any interior physical surgical site, where the virtual surgical site on screen 726 is not based on any physical corresponding site. In a different example, the virtual surgical site shown on screen 726 can correspond at least partially to a physical site included within the model 720. The simulation processing component 102 can be located in one or more of the components of system 700, such as the surgeon console 704, the patient side cart 706, etc., or can be located in its own housing (not shown).

Figure 7B:
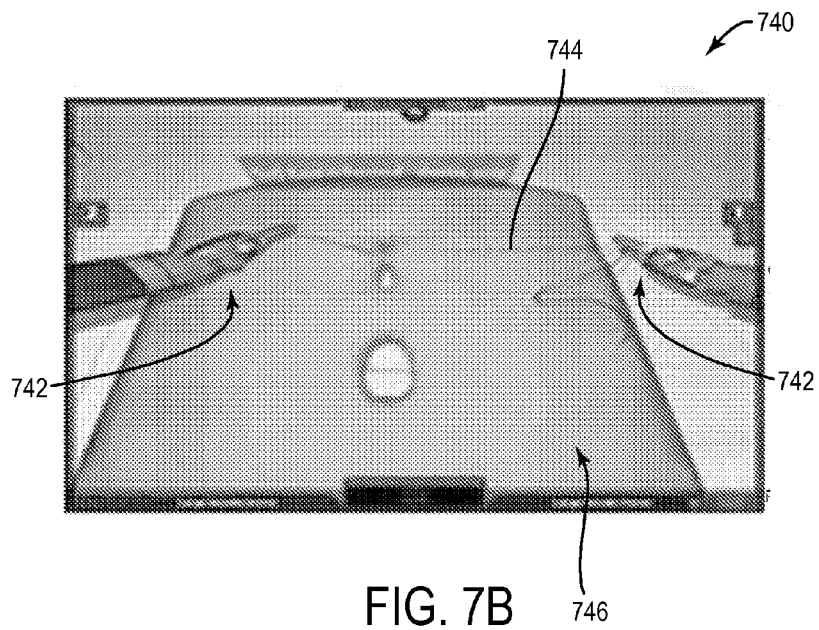
FIG. 7B shows an example display screen provided on the surgeon console of FIG. 7A.

In FIG. 7B, an example display screen 740 is shown that is provided on the surgeon console 704. In some implementations, two stereoscopic display screens 740 can be provided to show a 3-D view, and/or screen 740 can be a touch-responsive screen. In this example, display screen 740 displays a virtual environment generated by the simulation processing component 104. For example, virtual instrument tips 742 (e.g., end effectors or other end portions) are displayed and are moved on the display screen 740 based on user manipulation of the controls at console 704. These displayed virtual instrument tips 742 also track the physical instrument tips at the patient side cart 706, which are moved within the model 720. Objects in the environment are also displayed, such as a thread 744 grasped by the instrument tips 742 used in suturing a portion of the object 746. In some implementations, the virtual thread is generated within the virtual environment, and/or the object 746 is generated as a new virtual object different from any physical objects within the model 720. In other implementations, the virtual thread 744 can correspond to a physical thread being manipulated within the model 720 by the physical instrument tips. Similarly, the manipulated object 746 can also correspond to a physical object within the model 720, In some implementations, as shown in FIG. 7A, the display screen 726 on the vision side cart 708 can display the same environment displayed on the screen 740 of the console 704. This allows an assistant user to view the scene that the console user is viewing, allowing greater assistance during the operation procedure.

In other implementations, an endoscope or other imaging device on the patient side cart 706 can capture images of the physical site within the model 720, and these images of the actual physical site can be displayed on display screen 740 and and/or display screen 726 instead of a generated virtual environment, or in combination with some virtual, generated objects.

Figure 8:
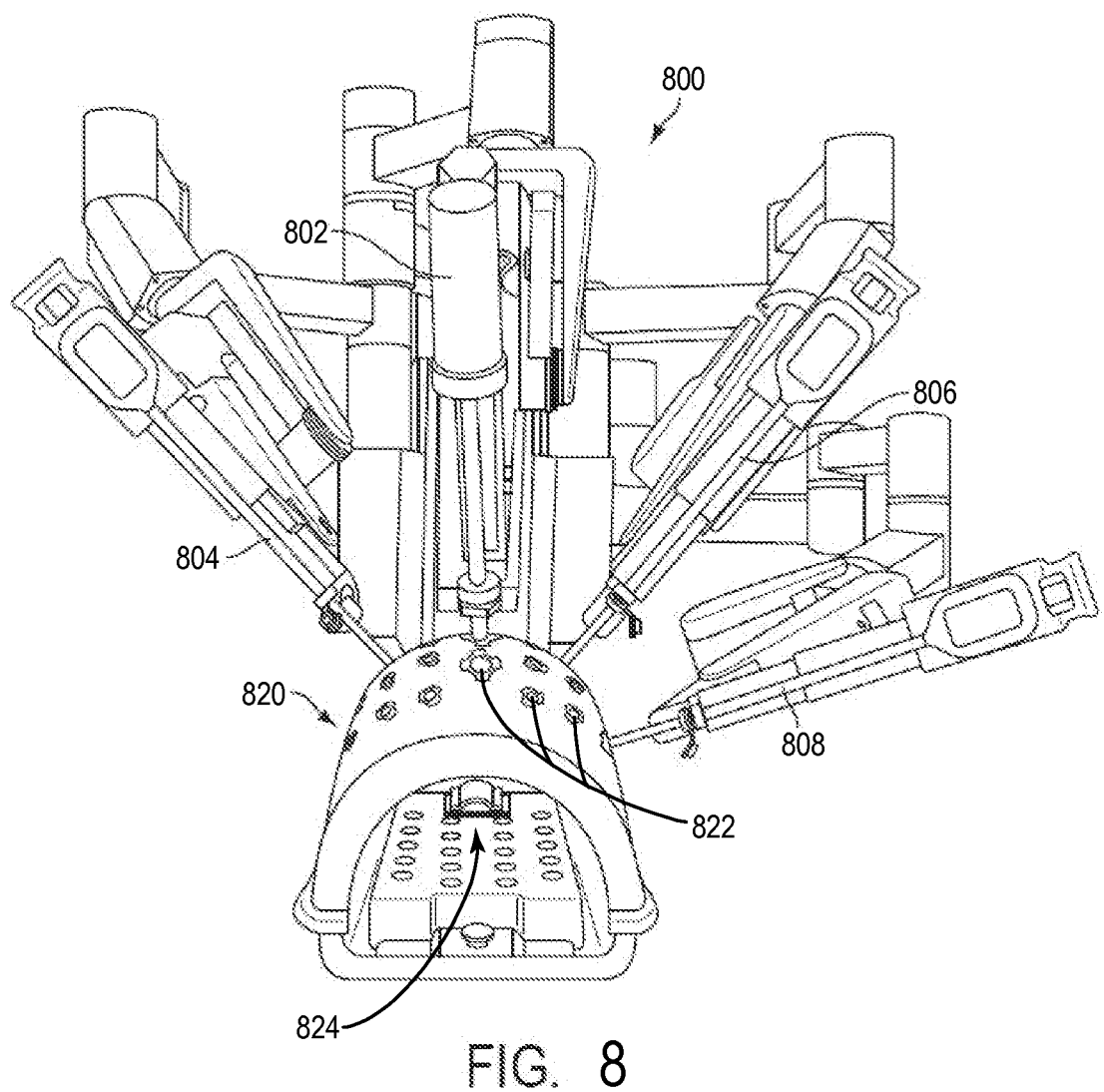
FIG. 8 is a perspective view of an example teleoperated medical device and anatomical model.

FIG. 8 is a perspective view of an example teleoperated medical device 800 that can be included in the patient side cart 106, similar to the patient side cart 706 shown in FIG. 7A, and an example anatomical model. Device 800 can include multiple manipulator arms, where each arm is coupled to one or more surgical instruments. For example, each arm can be considered a teleoperated manipulator that can be coupled ("docked") to each port or cannula in a model for patient, and the manipulator controls both the cannula and the instrument that extends through the cannula and into the model or patient to reach the physical surgical site. For example, one instrument 802 can be a camera or endoscope instrument and the three other instruments 804, 806, 808 can be surgical operation instruments.

An example of an anatomical model 820 is shown, used to enhance the simulation of working on a patient in a surgical operating room environment. Model 820 can include multiple holes 822 and a top surface simulating a surface of a patient and through which cannulas and surgical instruments are inserted. In some implementations, one cannula and instrument can be inserted in each hole, while in other implementations, multiple cannulas and/or instruments can be inserted through a single hole (e.g., single-site). The model 820 can include a hollow space underneath or within, which can hold one or more physical surgical sites 824 at which physical exercises can take place manipulating exercise objects, such as flexible materials, thread, beads on wires, etc.

Model 820 is placed on an operating table (such as table 722 described above) at a location corresponding to a patient's position on the table. In some implementations of setup simulation procedures, different surgical operations may require various different port placements, and a user being trained may have to position the device 800 in one location for one surgical operation (e.g., at the foot of the operating table, simulating a location between the patient's legs) and in a second location for another surgical operation (e.g., to the side the operating table). Some examples of anatomical model 820 and exercises are described in copending patent application Ser. No. 13/968,253, entitled, "Anatomical Model and Method for Surgical Training," which is incorporated herein by reference in its entirety.

Figure 9A:
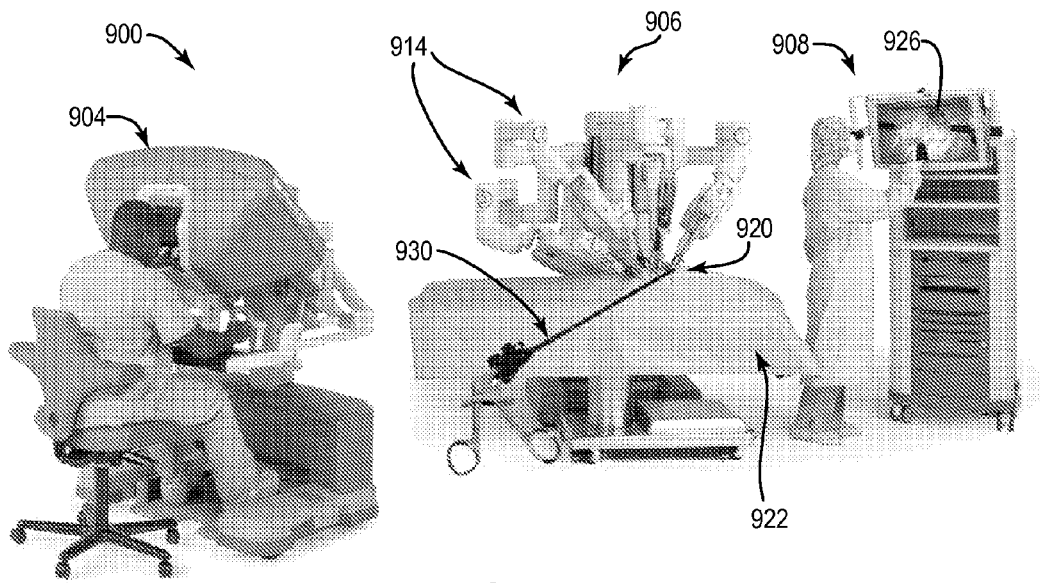
FIG. 9A shows another example simulation system including examples of several components described herein.

FIG. 9A shows another example 900 of a simulation system including examples of several of the components described herein. Similarly to FIG. 7A, a surgeon console 904 can provide controls for a user and can also include one or more display screens (example shown in FIG. 9B). A patient side cart 906 includes a number of manipulator arms 914 which include surgical instruments at the ends of the arms and which are responsive to the controls operated by the user at the surgeon console 904. An operating room table 922 is positioned adjacent to the patient side cart 906, and can include an anatomical model 920 similarly as described above. A vision side cart 908 can include a display screen 926 and other components, such as electronic equipment. In this example, the display screen 926 displays a virtual environment similar to the environment displayed on the screen of the surgeon console as described below in FIG. 9B. A component corresponding to simulation processing component 102 can be located in one or more of the components of system 900 similarly as described above.

Simulation system 900 can also include manual surgical instruments, such as manual instrument 930 which is shown as a laparoscopic instrument. In some implementations, a manual instrument 930 can be guided and manipulated by an assistant user into or relative to model 920 during simulated surgical operations, while a surgeon user controls teleoperated surgical instruments using the surgeon console 904. The surgeon trainee an assistant trainee can train together during a simulation. In other implementations, the surgeon trainee can operate the surgeon console 904 and can operate one or more manual instruments 930, e.g. Where one or more telemanipulated instruments can be operated by the simulation system (e.g., an endoscopic instrument). Some implementations can enable the simulation of a surgical operation using teleoperated instruments, and then enable the simulation of that same surgical operation using one or more manual instruments. The results of these two simulations can then be compared by the system, and results summarized. Some implementations including manual instrument 930 are described below.

Figure 9B:
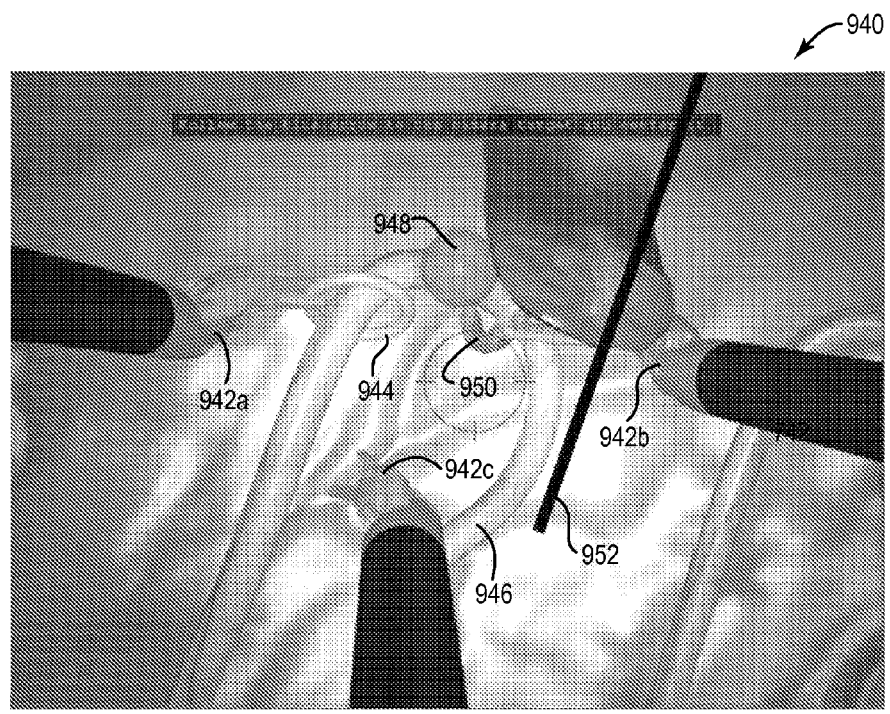
FIG. 9B shows an example display screen provided on the surgeon console of FIG. 9A.

In FIG. 9B, an example display screen 940 is shown that can be provided on the surgeon console 904. In this example, display screen 940 displays a virtual environment generated by the simulation processing component 104, which can be a 2D or 3D environment, and can be displayed on a touch-responsive screen in some implementations. In this example, the virtual environment presents a realistic background of the interior simulating an actual patient surgical site within an actual patient, including body tissue and other body components instead of the generated exercise environment of FIG. 7B. Virtual instrument tips 942 are displayed and are moved on the display screen 940 based on user manipulation of the controls at console 904. The displayed instrument tips 942 also track the physical instrument tips of the patient side cart 906, which are moved at a physical surgical site within the model 920.

Objects in the virtual environment are also displayed, such as a ring 944 grasped by an instrument tip or end effector 942a and moved along a track 946 following a virtual object 948 as an exercise. In some implementations, the ring 944 and wire track 946 can have physical corresponding objects provided in the model 920 which are manipulated by the physical instruments corresponding to the virtual instruments 942. In other implementations, there need not be corresponding physical objects to one or more of the virtual objects. For example, none of the virtual objects need correspond to physical instruments, where the physical instruments of the patient side cart can be dummy instruments. Or, just the virtual instruments can correspond with physical instruments, which interact with nothing in the model.

For example, instrument tip 942b can be grasping a virtual object 950 which has no physical corresponding object at the physical site in the model 920. In some implementations, haptic output can be provided on the controls of the surgeon console 904 using one or more actuators of the surgeon console, to provide the user the sensation of manipulating the object 950.

In some implementations, an instrument tip 952 can be displayed on screen 840 and within the virtual environment. For example, tip 952 can correspond to a manual instrument, such as manual instrument 930 shown in FIG. 9A, that has been inserted in the anatomical model 920. The physical end or tip of instrument 930 can be tracked within model 920 as described in some implementations herein, and its corresponding virtual tip 952 moved accordingly within the virtual environment of screen 940. For example, the virtual tip 952 can be displayed to interact with virtual objects that correspond with physical objects in the model 920, and/or with virtual objects with no corresponding physical objects.

Figure 10A:
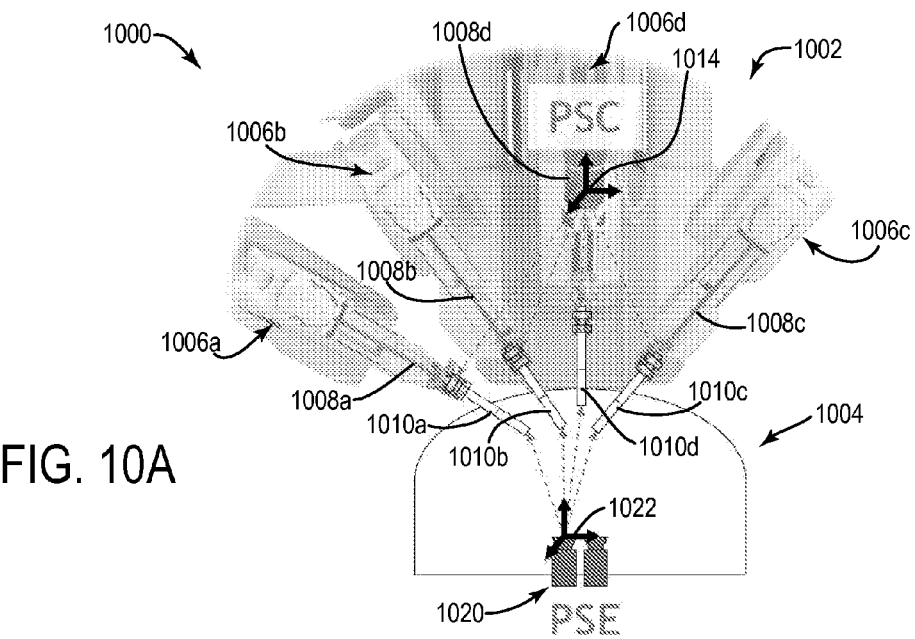
FIGS. 10A-10C illustrate examples related to tracking instruments within an anatomical model.
Figure 10B:
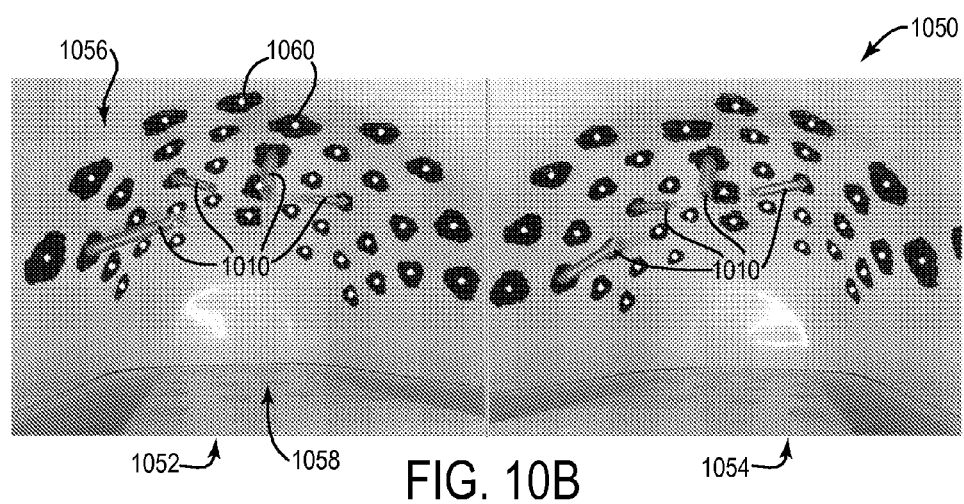
Figure 10C:
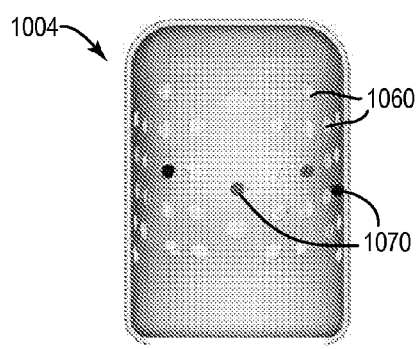

FIGS. 10A-10C illustrate examples related to tracking instruments within an anatomical model. FIG. 10A is a diagrammatic illustration of an example implementation 1000 of a patient side cart 1002 and an anatomical model 1004. Manipulator arms 1006a, 1006b, and 1006c of the patient side cart 1002 include operating instruments that are surgical instruments 1008a, 1008b, and 1008c, respectively, and manipulator arm 1006d includes an operating instrument that is an endoscopic instrument 1008d. Each of the instruments 1008a-d is inserted in an associated cannula 1010a, 1010b, 1010c, or 1010d, respectively (e.g., the instrument can be a trocar within a cannula 1010, or a cannula 1010 can be part of a trocar 1008 in some examples, such as for an initial insertion in the model 1010). The cannulas 1010 are inserted in apertures of the model 1004.

For example, the endoscope instrument 1008d can have its own sensing reference origin 1014 relative to which it can sense the instruments and cannulas inserted in the model 1004. For example, the endoscope camera can capture images of the cannulas 1010 within the model when they are moved into the view of the camera.

The model 1004 can also include its own sensing system for tracking instruments inserted in (or otherwise interacting with) the model 1004. In the example implementation of FIG. 10A, one or more sensors are provided within the model 1004 to sense the cannulas 1010. In this example, a camera system 1020 is positioned on the interior base of the model 1004 to sense the interior of the model 1004. For example, a camera system 1020 can be positioned near or within a patient side element (PSE) such as model 1004, or can be positioned at other locations of the bottom or sides of the model. Camera system 1020 thus continually capture images showing the positions of cannulas 1010 being inserted in the model, as well as images showing the positions of surgical instruments 1008 inserted through the cannulas 1010. Camera system 1020 thus has its own sensing reference origin 1022 which is the reference point for images captured by the camera system. In the example of FIG. 10A, two cameras are shown in the camera system 1020 to allow stereo triangulation in determining positions of the cannulas 1010 in the anatomic model. In other implementations, camera system 1020 can include a single camera, or other types of sensors to capture position or motion of cannulas and instruments.

FIG. 10B shows example views 1050 of a camera system within an anatomical model, such as camera system 1020 with an model 1004 of FIG. 10A. The camera system 1020 includes two cameras, and a left view 1052 is the view of one of the cameras, and a right view 1054 is the view of the other camera. The top surface 1056 and bottom surface 1058 are shown, as well as apertures 1060 in the top of the model. Cannulas 1010 can be viewed inserted through specific holes of the model. In this example having two cameras, stereo triangulation can be used to accurately determine the position of each cannula 1010 with reference to the origin system of the cameras. In some implementations, each cannula 1010 can be distinguished from each other cannula 1010 with individual marks or other characteristics. For example, each cannula 1010 can have a different exterior color to allow easy distinguishment of each cannula 1010 by the sensing system 1020.

FIG. 10C shows a plan view of the external surface of the top surface of model 1004, including holes 1060 in the surface. Marks 1070 indicate particular holes through which the cannulas 1010 were detected by the camera system 1020 to have been inserted. Such a view can be created by the simulation processing component 104 based on the sensing views of the camera system 1020 and (for example) a 3-D computer-aided design (CAD) model of the anatomical model 1004 used in visualization software. The view of FIG. 10C can be used to display port placement for the model for instructional or guidance purposes during a simulated medical procedure. For example, the view showing marked used ports can be displayed next to a similar view that displays the correct ports to be used in the particular medical procedure being simulated.

Manual instruments can be tracked by sensing system 1020 similarly to the cannulas and teleoperated instruments described above. For example, a manual laparoscopic tool can be tracked. Other instruments can include a uterine manipulator, retraction tool, needle-passing tools, another manipulator arm or instrument attached to a separate component of the simulation system, or other instruments where an instrument or device separate from the patient side cart is being tracked and incorporated into the simulation environment.

Figure 11A:
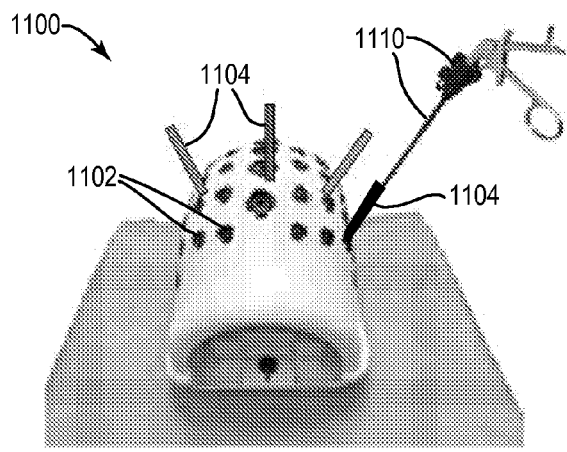
FIGS. 11A and 11B are diagrammatic illustrations of one example of the use of an anatomical model in simulated medical procedures that include the use of both teleoperated and manual surgical instruments.
Figure 11B:
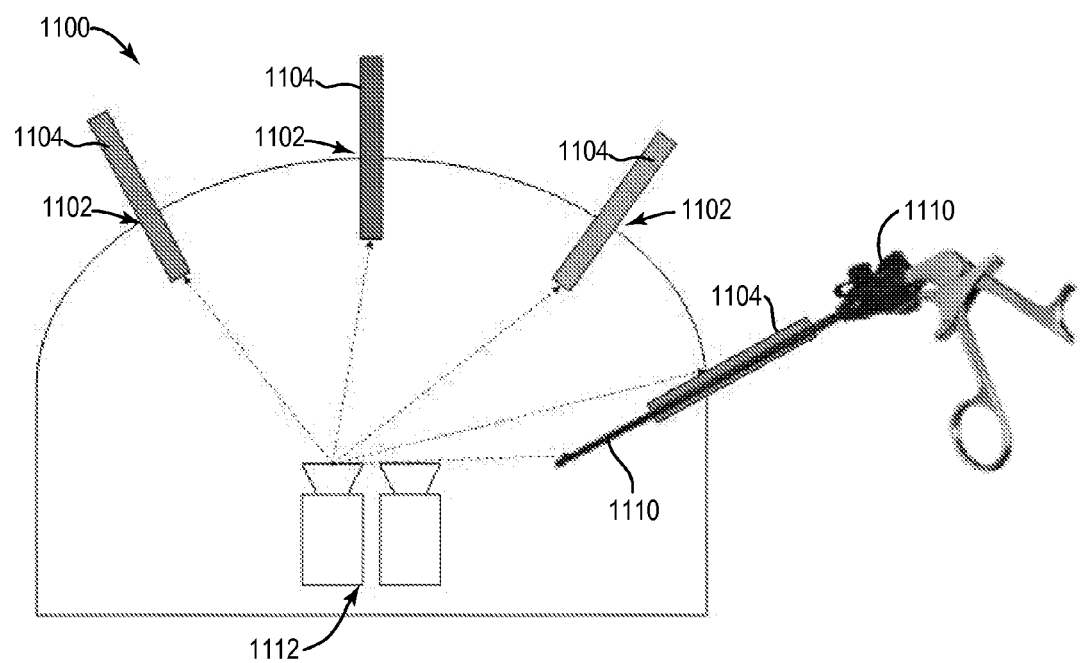

FIGS. 11A and 11B are diagrammatic illustrations of one example of the use of an anatomical model 1100 in simulated medical procedures that includes the use of both teleoperated and manual surgical instruments. FIG. 11A is an exterior view of the model 1100 and inserted instruments, and FIG. 11B is an interior view of the model 1100. Model 1100 can be similar to models described above and includes apertures 1102 in an upper shelf portion of the model, through which cannulas 1104 have been inserted during a setup procedure. Teleoperated surgical instruments, such as laparoscopic instruments and endoscopes, can be inserted in the cannulas 1104. Alternatively, manual surgical instruments, such as manual laparoscopic instrument 1110, can be inserted in one or more of the cannulas 1104.

In this implementation, sensors can be provided within the model 1100 to sense the cannulas 1104 and manual instruments such as instrument 1110. In this example, camera system 1112 is positioned on the interior base of the model 1100 to sense the interior of the model 1100 similarly as described for FIG. 10A. Camera system 1112 can thus capture images showing when cannulas 1104 have been inserted in the model, as well as images showing when surgical instruments have been inserted in the cannulas 1104. In some implementations, since the positions of teleoperated surgical instruments are already known based on sensors in the teleoperated arms, such instruments do not need to be tracked, and dummy instruments can be used, e.g., which do not extend into the interior hollow portion of model 1100.

Other types of sensors instead of cameras can be used in other implementations. For example, electromagnetic sensors, other optical sensors, etc. can be used to sense cannulas and manual surgical instruments.

Figure 12:
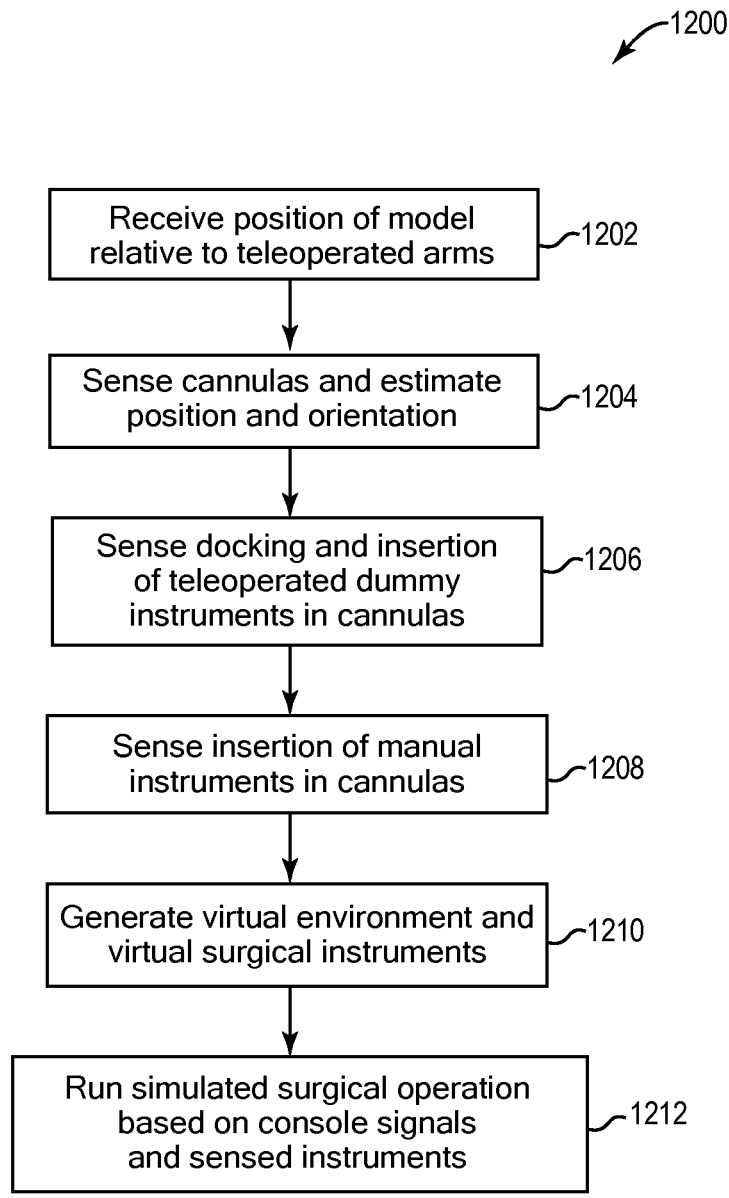
FIG. 12 is a flow diagram illustrating an example method for using an anatomical model with reference to FIGS. 11A-11B.

FIG. 12 is a flow diagram illustrating an example method for using an anatomical model with both teleoperated surgical instruments and manual surgical instruments in one or more simulated surgical procedures, with reference to FIGS. 11A-11B. In some implementations, blocks 1202 to 1208 can be performed during a simulated setup procedure, and blocks 1210 and 1212 can be performed during a simulated surgical operation (block 1210 can also be performed during a simulated setup procedure).

In block 1202, the simulation processing component 102 can receive a position of the model 1100 relative to the teleoperated arms of the patient side cart. For example, a teleoperated instrument at the end of one of the arms can be moved to contact (register) the model in multiple locations to establish the location of the mode in 3-D space. In other implementations, block 1202 can be omitted or performed at a later time, e.g., the model location can be determined relative to the teleoperated instruments after docking instruments to cannulas in block 1206 below by using sensors in the teleoperated arms.

In block 1204, the simulation processing component senses the insertion of cannulas 1104 in the model 1100 and the simulation processing component estimates the position and orientation of the cannulas 1104. For example, sensors like camera system 1112 can send signals to the simulation processing component. In block 1206, the simulation processing component senses docking and insertion of teleoperated dummy instruments in cannulas 1104, e.g., based on signals from the sensors in the manipulator arms of the patient side cart. In other implementations, full surgical instruments can be docked and inserted in the cannulas 1104. In block 1208, the sensors (such as camera system 1112) and simulation processing component sense insertion of one or more manual instruments in cannulas 1104, such as instrument 1110. Blocks 1206 and 1208 can be performed in any order and/or at least partially simultaneously. In block 1210, the simulation processing component generates a virtual environment and generates virtual surgical instruments in the virtual environment corresponding to the teleoperated surgical instruments and the manual surgical instruments. In block 1212, the simulation processing component runs the simulated surgical operation based on console signals, sensed teleoperated instruments, and sensed manual surgical instruments.

Some implementations of method 1200 can use the sensing system of the anatomical model and/or the teleoperated medical device in conjunction with displaying a virtual environment. In some examples, a generic picture of the model can be displayed without the teleoperated arms and without the exact position/orientation of the model relative to teleoperated arms. For example, the port locations placed by a user can be identified using cameras inside the model without using the teleoperated arm kinematics. Instruction can be given to the user to adjust incorrect port locations before beginning to dock the teleoperated arms to the model. Once docked, the arm kinematics can be used to estimate the position and orientation of the model relative to the teleoperated medical device. (Other implementations can use sensors placed in or on the anatomical model to estimate the pose and location of the model relative to the patient side cart, rather than using the teleoperated arm sensors.) An entire scene of the surgical site and/or operating room can then be displayed to trainees. In some implementations, sensors in the model can track surgical instruments to provide an estimate of where the model is relative to the teleoperated device and this estimate of location can be updated during a procedure or operation to continuously provide accurate relative model location in case the model is bumped or moved by trainees.

Figure 13A:
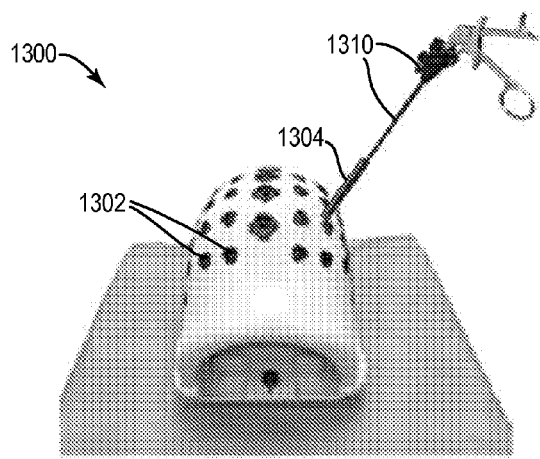
FIGS. 13A and 13B are diagrammatic illustrations of a second example of the use of an anatomical model in simulated medical procedures that include the use of manual surgical instruments.
Figure 13B:
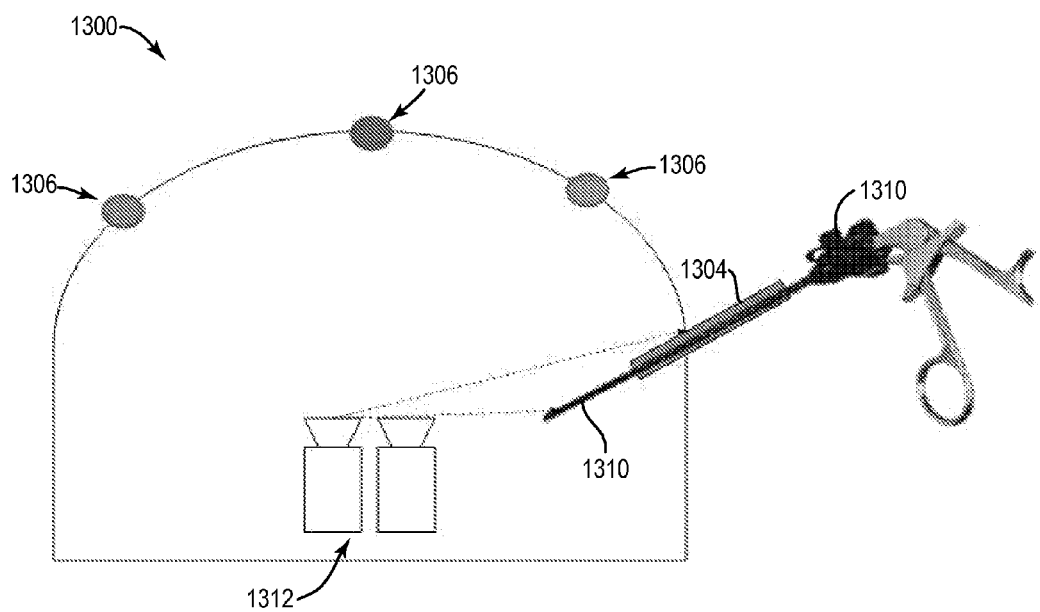

FIGS. 13A and 13B are diagrammatic illustrations of an example of the use of an anatomical model 1300 in simulated medical procedures that include the use of manual surgical instruments. Model 1300 can be similar to the models described above. FIG. 13A is an exterior view of the model 1300 and an inserted instrument, and FIG. 13B is an interior view of the model 1300. Model 1300 includes apertures 1302 in an upper portion of the model. Particular apertures 1306 can be designated as remote centers for teleoperated instruments typically inserted through these apertures, but no cannulas for teleoperated instruments need be placed in this implementation. One or more cannulas, such as cannula 1304, are inserted in model 1300 during a setup procedure in apertures where manual instruments are to be inserted. Manual surgical instruments, such as manual laparoscopic instrument 1310, can be inserted in the cannula 1304.

Sensors can be provided within the model 1300 to sense the cannulas such as cannula 1304 and manual instruments such as instrument 1310. In this example, camera system 1312 is positioned on the interior base of the model 1300 to sense the interior of the model 1300. Camera system 1312 can capture images showing when cannula 1304 has been inserted in the model, as well as images showing when manual surgical instruments have been inserted in the cannula 1304. The apertures 1306 for teleoperated surgical instruments can be located by the simulation processor based on the known geometry of the model and the particular medical procedure being simulated. Thus these particular aperture locations can be assumed arm remote centers, and no cannulas need to be tracked, nor do any teleoperated surgical instruments need to be docked with the model. Thus this implementation can be used for simulations that include the use of manual surgical instruments and do not need use of a patient side cart, e.g., the teleoperated surgical instruments can all be virtual instruments generated in a virtual environment provided by the simulation processing component.

Other types of sensors instead of cameras can be used in other implementations. For example, electromagnetic sensors, other optical sensors, etc. can be used to sense cannulas and manual surgical instruments.

Figure 14:
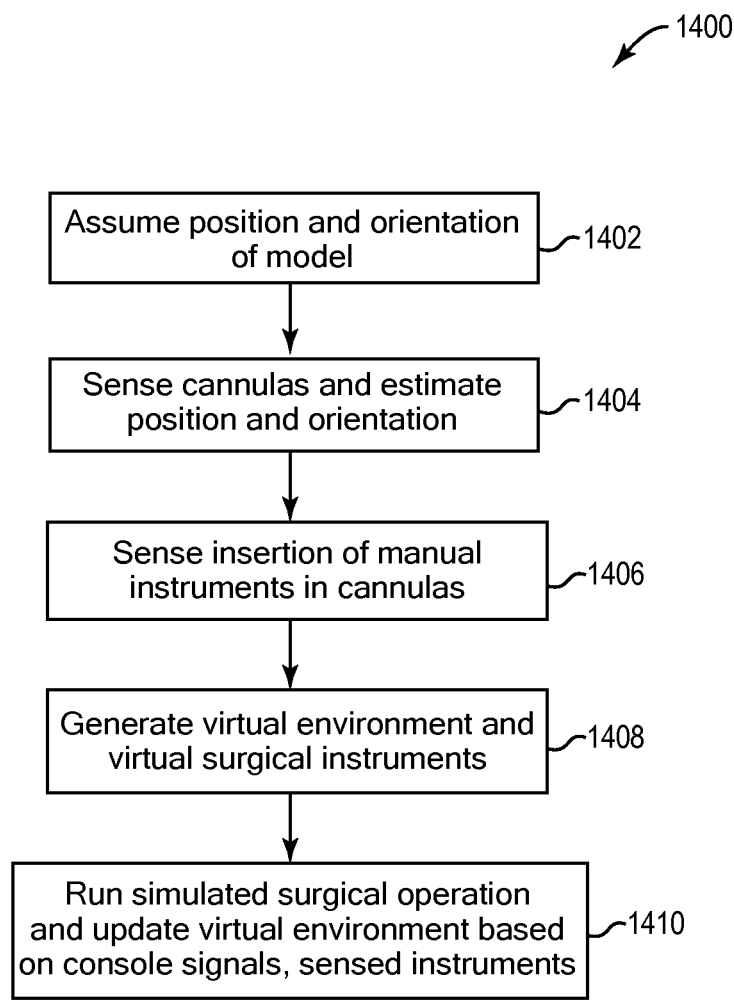
FIG. 14 is a flow diagram that illustrates an example method for using an anatomical model with reference to FIGS. 13A-13B.

FIG. 14 is a flow diagram illustrating an example method 1400 for using manual surgical instruments in a simulated medical procedure, with reference to FIG. 13. In some implementations, blocks 1402 to 1406 can be performed during a simulated setup procedure, and blocks 1408 and 1410 can be performed during a simulated surgical operation (block 1408 can also be performed during a setup procedure).

In block 1402, the simulation processing component 102 assumes the position and orientation of the model 1300, including assuming the positions of the surgical site and the apertures in the model (remote centers of teleoperated instruments) through which teleoperated surgical instruments would be inserted. To do this, the simulation processing component knows the geometry of the model and its apertures and physical surgical site location, as well as the particular apertures used in the surgical operation being set up. In block 1404, the simulation processing component senses the insertion of cannulas 1304 in the model 1300 using sensors of the model 1300 and the simulation processing component estimates the position and orientation of the cannulas 1304. In block 1406, the simulation processing component senses insertion of one or more manual instruments in cannulas 1304, such as instrument 1310. In block 1408, the simulation processing component generates a virtual environment and generates virtual surgical instruments in the virtual environment corresponding to teleoperated surgical instruments and the manual surgical instruments. The relative position between the manual surgical instruments and the assumed aperture locations for the teleoperated instruments in the model 1300 enable relative positioning of these instruments in the virtual environment. In block 1410, the simulation processing component runs the simulated surgical operation and updates the virtual environment based on console signals (to move the virtual teleoperated surgical instruments) and sensed manual surgical instruments.

Features described herein offer a wide variety of functionality and advantages in various simulation implementations. For example, a simulation processing component (e.g., processing unit) can interact with a surgeon console (e.g., with master controllers) and/or a patient side cart (e.g., with slave manipulator arms and instruments). The console master can drive the slave arms with or without instruments (or with dummy instruments) on the patient side cart.

The simulation system can simulate and provide guidance and other feedback on system setup and accurate positioning of the manipulator arms prior to a simulated surgical operation. This can be used to provide standardized and consistent training to surgeons using inanimate training exercises or wet-lab exercises. A simulated surgical operation can follow the simulated setup procedure, which can allow the entire medical procedure to be simulated. This allows trainees to see the consequences of improperly-performed tasks. For example, improper or incorrect tasks performed in a setup procedure may have repercussions in a following surgical operation, and the simulation system herein simulates this entire effect to allow trainees to learn and improve.

The simulation system can display a virtual environment (e.g., ignore endoscope feed and instruments if installed), combined or augmented environment (e.g., endoscope feed with generated graphical visual overlays or virtual environment objects), or entirely visual imaging (e.g., endoscopic) feed. For example, some implementations can display the virtual environment and/or endoscopic video feed from the patient side cart on the surgeon console display screen and on one or more external display screens (e.g., in 2D or 3D). In some examples, virtual or augmented images can be output through display systems (such as using TilePro from Intuitive Surgical, Inc.) on the surgeon console during any training exercise to provide instruction or performance metrics. For example, virtual reality (VR) or other generated images, and/or augmented reality (AR) ghost images overlaid on camera images, can be displayed on system display devices to indicate or highlight system areas of concern or interest, such as patient cart setup joints having incorrect positions highlighted, reachability limits of instruments displayed, and/or internal/external collisions. This can reduce the burden on training assistants to catch mistakes during training procedures.

The system can record the kinematics and events of the master console(s) and teleoperated slave medical device(s) during completion of inanimate training or wet-lab exercises by a console surgeon to compute training metrics and display such metrics using a similar interface as purely virtual training exercises. Additionally or alternatively, the system can record the kinematics and events of teleoperated devices during completion of patient-side exercises and setup procedures using actual instruments, and compute training metrics and display such metrics using a similar interface as purely virtual training exercises. Further, the system can record the kinematics and events of the masters and slaves during completion of exercise modules on porcine models (for example, during offsite training) to provide metrics and display such metrics. Such detailed collection of data and quantification and tracking of trainee performance allows trainees and simulation operators to review training progress in high detail, leading to insights and improvements in individual trainee progress as well as training procedures, and thus permits overall greater training effectiveness.

All data from any training environment or configuration can be recorded and stored locally or remotely in the same way to improve accessibility of data, monitoring of surgeon training and performance of trainee personnel during simulated procedures, standardization of exercises, and feedback to surgeon during training (e.g., to improve surgeon training). The simulation system can centralize most training content to one software platform separate from the system architecture, which can avoid difficulties of changing system software to accommodate training (potentially leading to FDA issues, etc.).

Teleoperated medical device surgery offers an unprecedented ability to record, track, and monitor surgery and surgeon training unlike any pre-existing form of surgery. Implementations described herein can make effective use of this capability and the data that can be harvested e.g., for simulation and training purposes. Some additional advantages of various implementations of teleoperated and non-teleoperated systems can include the following.

Features described herein can centralize user training and evaluation on a single system, e.g., a single teleoperated medical system. Some systems can provide the ability to use a single simulation framework on teleoperated medical system with a separate surgeon console and patient side cart to monitor and track progress and to display feedback all under a single software and user interface (UI) framework. Some systems can provide the ability to provide augmented reality output and feedback during wet-lab or porcine model exercises and dry-lab exercises using a teleoperated medical system. Some systems can provide the ability to combine training data using a single software and hardware architecture used for various types of training exercises including virtual environment exercises, inanimate exercises, wet-lab or porcine models, etc. One or more features can allow any training exercise or offsite lab exercise to be conducted using the single simulation architecture to provide real-time (during a procedure) and end-of-exercise metrics to guide training and learning.

Features herein can improve accessibility of training data, especially for tasks not normally implemented on a simulator system. Features can improve standardization of training since the system can be used for several types of training tasks. Features can improve surgeon training at offsite training labs by quantifying and delivering feedback in addition to that provided by training personnel to help trainees learn. Also, features can help training personnel to better manage multiple surgeon trainings simultaneously (e.g., dual surgeon console trainings). Furthermore, features can improve surgeon training conducted by clinical sales representatives (CSRs) or other instructors by simulating tasks performed during setup procedures, and by providing feedback determined by the system and displayed in real-time for setup exercises.

Features described herein can expand the capability of teleoperated and non-teleoperated medical simulation systems to support inanimate training exercises, wet-lab training scenarios, and VR-based training exercises. A single simulation system can administer and record all training performed by surgeons, e.g., with their CSRs, with dedicated training specialists (TSs), or independently. The simulation system can be used to simulate all interactions with the system outside of actual surgery.

It should be noted that the blocks described in the various methods herein can be performed in a different order than shown and/or simultaneously (partially or completely) with other blocks in the same method (or other methods), where appropriate. In some implementations, blocks can occur multiple times, in a different order, and/or at different times in the methods.

This description and the accompanying drawings that illustrate features and implementations should not be taken as limiting. Various mechanical, compositional, structural, electrical, and operational changes may be made without departing from the spirit and scope of this description and the claims. In some instances, well-known circuits, structures, or techniques have not been shown or described in detail in order not to obscure described features.

Further, this description's terminology is not intended to limit the scope of the claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. Components described as coupled may be electrically or mechanically directly coupled, or they may be indirectly coupled via one or more intermediate components.

Elements described in detail with reference to one implementation may, whenever practical, be included in other implementations in which they are not specifically shown or described unless the one or more elements would make an implementation non-functional or provide conflicting functions. For example, if an element is described in detail with reference to one embodiment and is not described with reference to a second embodiment, the element may nevertheless be included in the second embodiment.

The functional methods, blocks, features, devices, and systems described in the present disclosure may be integrated or divided into different combinations as would be known to those skilled in the art. Disclosed methods and operations may be presented in a specific order, but the order may be changed in different particular implementations. In some implementations, multiple steps or blocks shown as sequential in this disclosure may be performed at least partially at the same time.

We claim:

1. A system comprising:
    a simulation processing component including at least one processor; and
    a medical device structure including a manipulator arm and a surgical instrument connected to the manipulator arm, wherein the medical device structure is positioned in a simulation area relative to a physical surgical site, wherein the medical device structure includes a medical device cart that supports the manipulator arm,
    wherein the simulation processing component is configured to perform operations in a simulated setup procedure, the operations in the simulated setup procedure comprising:
        determining a position in the simulation area of the medical device cart relative to the physical surgical site;
        comparing the position of the medical device cart to a reference position;
        causing output of setup feedback information by a first output device based on a result of comparing the position of the medical device cart;
        receiving arm position signals that indicate positions of the manipulator arm, wherein the manipulator arm and the surgical instrument are positioned in space by at least one user in setup tasks during the simulated setup procedure;
        comparing the positions of the manipulator arm to reference arm positions; and
        causing output of additional setup feedback information by the first output device based on a result of comparing the positions of the manipulator arm,
    wherein the simulation processing component is configured to perform operations in a simulated surgical procedure that is performed based on a resulting position of the medical device structure resulting from the simulated setup procedure, the operations in the simulated surgical procedure comprising:
        reading position signals for the manipulator arm that describe at least one of a position or a configuration of the surgical instrument relative to the physical surgical site, wherein the at least one of the position or the configuration are based on control signals corresponding to inputs by a user of the system.

2. The system of claim 1, wherein the operations in the simulated setup procedure include one or more of:
    determining whether one or more particular joints of the manipulator arm are incorrectly positioned relative to reference joint positions; or
    determining whether the manipulator arm is positioned at a particular position during movement of the medical device cart in the simulation area.

3. The system of claim 1, wherein the operations in the simulated surgical procedure further comprise:
    comparing the at least one of the position or the configuration of the surgical instrument to an instrument reference position or configuration; and
    causing output of surgical feedback information by a second output device, wherein the surgical feedback information is based on a result of the comparing the at least one of the position or the configuration of the surgical instrument,
    wherein the physical surgical site comprises an anatomical model, wherein the anatomical model comprises at least one sensor operative to output sensor signals to the simulation processing component indicative of a position of the surgical instrument relative to the anatomical model.

4. The system of claim 1, wherein the operations in the simulated surgical procedure further comprise:
    determining whether an incorrect setup is present during the simulated surgical procedure based on the position of the medical device cart and the positions of the manipulator arm; and
    in response to determining that the incorrect setup is present, causing output of surgical feedback information by the first output device to indicate an effect of the incorrect setup on the simulated surgical procedure.

5. The system of claim 1, further comprising a control console including at least one input control operable by the user to generate the control signals that are input to the simulation processing component during the simulated surgical procedure, wherein a second output device includes a display device included in the control console, wherein the control console is a standalone component moveable in the simulation area independently of the physical surgical site and of the medical device structure, wherein the operations in the simulated setup procedure further comprise:
  determining a position of the control console in the simulation area;
  comparing the position of the control console to a reference position for the control console; and
  causing output of additional setup feedback information by the first output device based on a result of comparing the position of the control console.

6. The system of claim 1, wherein the operations in the simulated surgical procedure further comprise:
  generating a virtual environment based on the position signals for the manipulator arm;
  updating the virtual environment according to changes in the position signals and according to the control signals, the updating comprising moving a virtual surgical instrument within the virtual environment, wherein an interaction of the virtual surgical instrument with a virtual surgical site of the virtual environment is defined at least partly by a physical relationship between the surgical instrument and the physical surgical site; and
  causing output by a second output device of a representation of a current state of the virtual environment.

7. The system of claim 1, wherein the medical device cart is a standalone component moveable in the simulation area independently of the physical surgical site.

8. A system comprising:
  a simulation processing component including at least one processor;
  a medical device structure including a manipulator arm and a surgical instrument connected to the manipulator arm, wherein the medical device structure is positioned in a simulation area relative to a physical surgical site; and
  a vision side cart including a display device, wherein the vision side cart is a standalone component moveable in the simulation area independently of the physical surgical site and of the medical device structure,
  wherein the simulation processing component is configured to perform operations in a simulated setup procedure, the operations in the simulated setup procedure comprising:
    determining a position of the medical device structure relative to the physical surgical site;
    comparing the position of the medical device structure to a reference position for the medical device structure;
    causing output of setup feedback information by a first output device based on a result of comparing the position of the medical device structure;
    determining a position of the vision side cart relative to the physical surgical site;
    comparing the position of the vision side cart to a reference position for the vision side cart relative to the physical surgical site and the medical device structure; and
    causing output of additional setup feedback information by the first output device based on a result of comparing the position of the vision side cart,
  wherein the simulation processing component is configured to perform operations in a simulated surgical procedure that is performed based on a resulting position of the medical device structure resulting from the simulated setup procedure, the operations in the simulated surgical procedure comprising:
    reading position signals for the manipulator arm that describe at least one of a position or a configuration of the surgical instrument relative to the physical surgical site, wherein the at least one of the position or the configuration are based on control signals corresponding to inputs by a user of the system.

9. A method comprising:
  coordinating a simulated medical procedure using a simulation processing component including at least one processor;
  in a simulated setup procedure of the simulated medical procedure, receiving position signals based on one or more positions of one or more manipulator arms of a teleoperable medical device moved by at least one user during the simulated medical procedure, wherein the one or more manipulator arms are physically positionable relative to a physical surgical site in order to perform a simulated surgical procedure, wherein at least one surgical instrument is coupled to at least one of the one or more manipulator arms, wherein the one or more manipulator arms and the at least one surgical instrument are positioned in space relative to the physical surgical site by the at least one user in setup tasks during the simulated setup procedure, wherein the teleoperable medical device includes a medical device cart and is a standalone component moveable in a simulation area independently of the physical surgical site;
  storing, in a storage device, the one or more positions of the one or more manipulator arms during the setup tasks of the simulated setup procedure;
  comparing the one or more positions during the setup tasks to one or more reference positions in reference tasks to evaluate a performance of the setup tasks of the simulated setup procedure; and
  causing output of feedback information using one or more output devices during the simulated setup procedure based on the evaluated performance of the setup tasks;
  receiving signals indicating a position of the medical device cart relative to the physical surgical site in a simulation area, wherein the medical device cart is positioned in the simulation area relative to the physical surgical site by the at least one user in the setup tasks during the simulated setup procedure;
  storing, in the storage device, the position of the medical device cart during the setup tasks of the simulated setup procedure; and
  comparing the position of the medical device cart to a reference position to evaluate the position of the medical device cart,
  wherein the feedback information is further based on comparing the position of the medical device cart.

10. The method of claim 9 further comprising, in a simulated surgical procedure of the simulated medical procedure, receiving second position signals based on one or more second positions of the one or more manipulator arms and the at least one surgical instrument during one or more surgical tasks performed by at least one trainee following the simulated setup procedure, wherein the one or more manipulator arms and the at least one surgical instrument of the teleoperated medical device are moved based on control signals provided by a surgeon console coupled to the teleoperated medical device, wherein the simulated surgical procedure is based on a configuration of the teleoperated medical device resulting from the simulated setup procedure.

11. A method comprising:
coordinating a simulated medical procedure using a simulation processing component including at least one processor;
in a simulated setup procedure of the simulated medical procedure, receiving position signals based on one or more positions of one or more manipulator arms of a teleoperable medical device moved by at least one trainee during the simulated medical procedure, wherein the one or more manipulator arms are physically positionable relative to a physical surgical site in order to perform a simulated surgical procedure, wherein at least one surgical instrument is coupled to at least one of the one or more manipulator arms, wherein the one or more manipulator arms and the at least one surgical instrument are positioned in space relative to the physical surgical site by the at least one trainee in setup tasks during the simulated setup procedure;
storing, in a storage device, the one or more positions of the one or more manipulator arms during the setup tasks of the simulated setup procedure;
comparing the one or more positions during the setup tasks to one or more reference positions in reference tasks to evaluate a performance of the setup tasks of the simulated setup procedure;
causing output of feedback information using one or more output devices during the simulated setup procedure based on the evaluated performance of the setup tasks;
in a simulated surgical procedure of the simulated medical procedure, receiving second position signals based on one or more second positions of the one or more manipulator arms and the at least one surgical instrument during one or more surgical tasks performed by at least one user following the simulated setup procedure, wherein the one or more manipulator arms and the at least one surgical instrument of the teleoperated medical device are moved based on control signals provided by a surgeon console coupled to the teleoperated medical device, wherein the simulated surgical procedure is based on a configuration of the teleoperated medical device resulting from the simulated setup procedure;
determining whether an incorrect setup is present during the simulated surgical procedure based on the one or more positions of the one or more manipulator arms; and
in response to determining that the incorrect setup is present, causing an output of surgical feedback information to indicate an effect of the incorrect setup on the simulated surgical procedure.

12. The method of claim 9, wherein the setup tasks include at least one of:
moving each of the one or more manipulator arms to a respective particular position;
installing the at least one surgical instrument on the at least one of the one or more manipulator arms; or
selecting one or more particular control functions on the teleoperable medical device for a simulated surgical procedure following the simulated setup procedure.

13. The method of claim 9, further comprising:
receiving signals indicating a position of a vision side cart relative to the physical surgical site in the simulation area, wherein the vision side cart is positioned in the simulation area relative to the physical surgical site by the at least one user in the setup tasks during the simulated setup procedure, wherein the vision side cart includes a display device, wherein the vision side cart is a standalone component moveable in the simulation area independently of the physical surgical site and of the medical device cart;
storing, in the storage device, the position of the vision side cart during the setup tasks of the simulated setup procedure; and
comparing the position of the vision side cart to a reference position to evaluate the position of the vision side cart,
wherein the feedback information is further based on comparing the position of the vision side cart.

14. The system of claim 7, wherein the medical device cart is positioned on a floor of the simulation area and the physical surgical site is provided on an operating table that is positioned on the floor of the simulation area.

15. A method to provide feedback in a simulated medical procedure, the method comprising:
performing operations in a simulated setup procedure, the operations in the simulated setup procedure comprising:
determining a position of a medical device structure relative to a physical surgical site, wherein the medical device structure includes a manipulator arm and a surgical instrument connected to the manipulator arm, wherein the medical device structure includes a medical device cart that supports the manipulator arm, wherein the medical device cart is positioned in a simulation area relative to the physical surgical site and the position of the medical device structure is the position of the medical device cart in the simulation area;
comparing the position of the medical device cart to a reference position;
causing output of setup feedback information by a first output device based on a result of comparing the position of the medical device cart;
receiving arm position signals that describe positions of the manipulator arm, wherein the manipulator arm and the surgical instrument are positioned in space by at least one user in setup tasks during the simulated setup procedure;
comparing the positions of the manipulator arm to reference arm positions; and
causing output of additional setup feedback information by the first output device based on a result of comparing the positions of the manipulator arm, and
performing operations in a simulated surgical procedure that is performed based on a resulting position of the medical device structure resulting from the simulated setup procedure, the operations in the simulated surgical procedure comprising:
reading position signals for the manipulator arm that describe at least one of a position or a configuration of the surgical instrument relative to the physical surgical site, wherein the at least one of the position or the configuration are based on control signals based on user input to a control device;
comparing the at least one of the position or the configuration of the surgical instrument to an instrument reference position or configuration; and
causing output of surgical feedback information by a second output device, wherein the surgical feedback information is based on a result of comparing the at least one of the position or the configuration of the surgical instrument.

16. The method of claim 15, wherein comparing the positions of the manipulator arm to reference arm positions includes one or more of:
  determining whether one or more particular joints of the manipulator arm are incorrectly positioned relative to reference joint positions; or
  determining whether the manipulator arm is positioned at a particular position during movement of the medical device cart in the simulation area.

17. The method of claim 15, wherein the operations in the simulated surgical procedure further comprise:
  determining whether an incorrect setup is present during the simulated surgical procedure based on the position of the medical device cart and the positions of the manipulator arm; and
  in response to determining that the incorrect setup is present, causing the surgical feedback information to indicate an effect of the incorrect setup on the simulated surgical procedure.

18. The method of claim 15, wherein the control device is a control console, and wherein the operations in the simulated setup procedure further comprise:
  determining a position of the control console in the simulation area, wherein the control console includes at least one input control operable by the user to generate the control signals during the simulated surgical procedure, wherein the second output device includes a display device included in the control console, wherein the control console is a standalone component moveable in the simulation area independently of the physical surgical site and of the medical device cart;
  comparing the position of the control console to a reference position for the control console; and
  causing output of additional setup feedback information by the first output device based on a result of comparing the position of the control console.

19. The method of claim 15, wherein the operations in the simulated setup procedure further comprise:
  determining a position of a vision side cart relative to the physical surgical site, wherein the vision side cart includes a display device, wherein the vision side cart is a standalone component moveable in the simulation area independently of the physical surgical site and of the medical device cart;
  comparing the position of the vision side cart to a reference position for the vision side cart relative to the physical surgical site and the medical device cart; and
  causing output of additional setup feedback information by the first output device based on a result of comparing the position of the vision side cart.

* * * * *